US007147762B2

(12) United States Patent
Bjellqvist et al.

(10) Patent No.: US 7,147,762 B2
(45) Date of Patent: Dec. 12, 2006

(54) METHOD OF ELECTROPHORESIS

(75) Inventors: Bengt Bjellqvist, Uppsala (SE); Ingmar Olsson, Uppsala (SE); Ronnie Palmgren, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 474 days.

(21) Appl. No.: 10/230,526

(22) Filed: Aug. 29, 2002

(65) Prior Publication Data
US 2003/0221963 A1 Dec. 4, 2003

(30) Foreign Application Priority Data
May 31, 2002 (SE) .................................. 0201655

(51) Int. Cl.
*G01N 27/26* (2006.01)
(52) U.S. Cl. .................... 204/461; 204/462; 204/468; 204/469; 204/612; 204/613
(58) Field of Classification Search ........ 204/450–470, 204/600–621
See application file for complete search history.

(56) References Cited
U.S. PATENT DOCUMENTS
4,124,638 A * 11/1978 Hansen ....................... 564/204

4,698,420 A * 10/1987 Urnovitz ................... 530/391.9
4,985,128 A * 1/1991 Ebersole et al. ............ 204/469
5,159,049 A * 10/1992 Allen ......................... 204/456
5,238,545 A * 8/1993 Yoshioka et al. ........... 204/462
6,638,408 B1 * 10/2003 Speicher et al. ............ 204/458

* cited by examiner

Primary Examiner—Nam Nguyen
Assistant Examiner—Jeffrey Barton
(74) Attorney, Agent, or Firm—Yonggang Ji

(57) ABSTRACT

The present invention relates a method of electrophoretic separation of protein and/or peptide components of a sample in a convection stabilized medium. More specifically, the method comprises the steps to contact the sample with the separation medium; to apply a voltage across said medium; and to observe the results by analysis of one or more sections of the separation medium. In the present method, a disulphide-comprising compound is added before or during the procedure to make an excess of reactive disulphide groups accessible to react with the cysteine groups of the proteins and/or peptides all through the separation procedure. The present invention also relates to electrophoretic separation media that comprises reactive disulphide groups, such as polyacrylamide gels, and the use of a solution that comprises reactive disulphide groups to pretreat an electrophoretic separation medium.

12 Claims, 10 Drawing Sheets

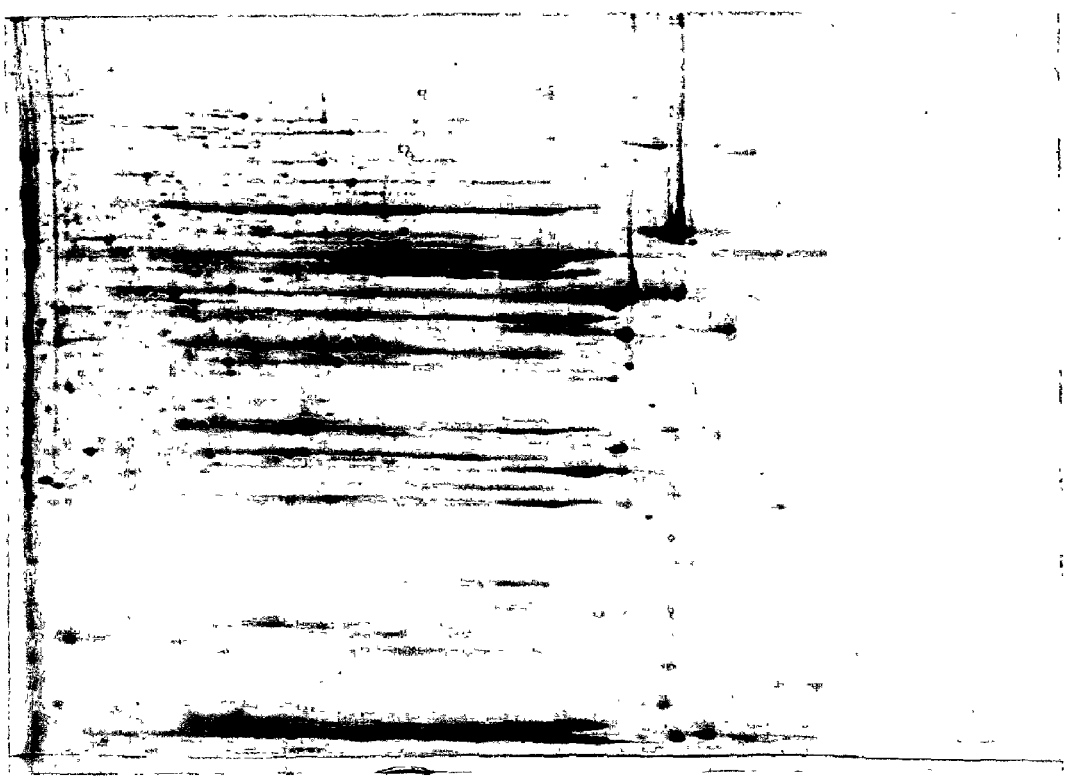
Figure 2a: 20 mM mercaptoethanol
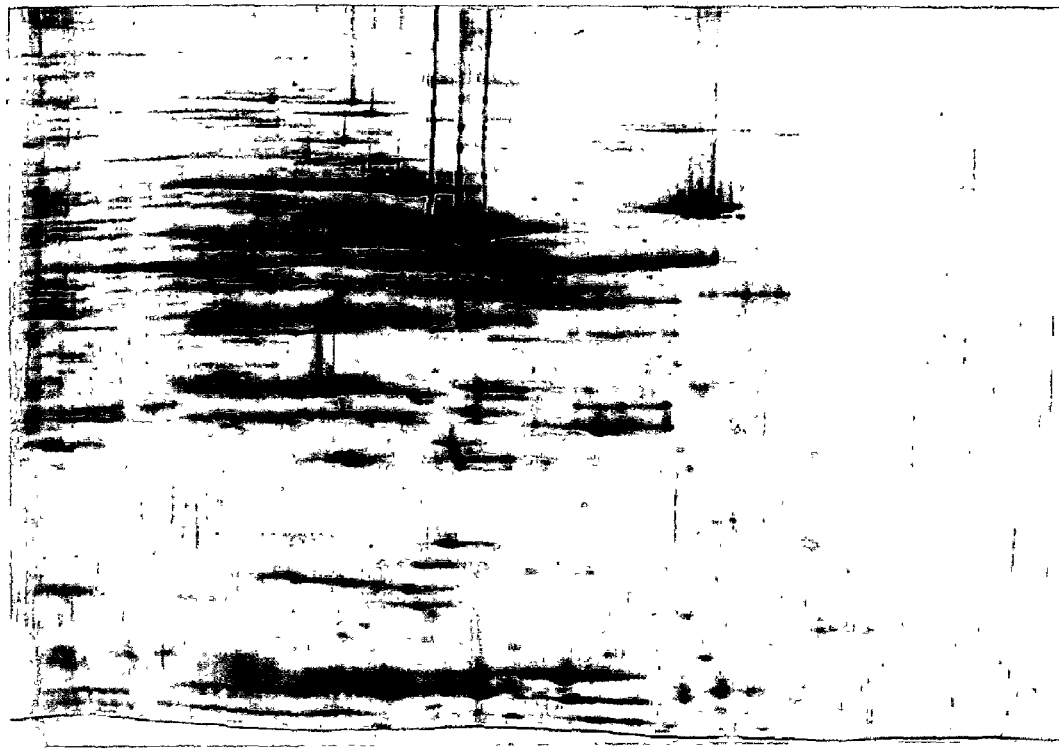
Figure 2b: IPG 20 mM DTT.

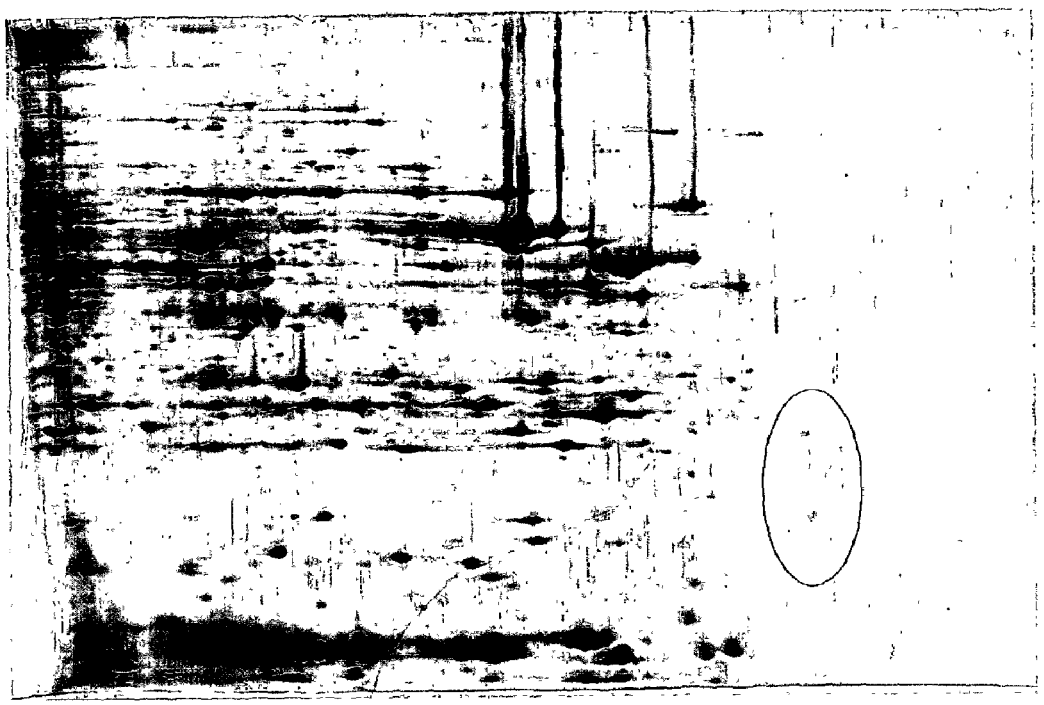
Figure 2c: 50 mM di-(2-hydroxyethyl)–disulfide
Note the reduction of streak compared to Figures 2a and 2b.
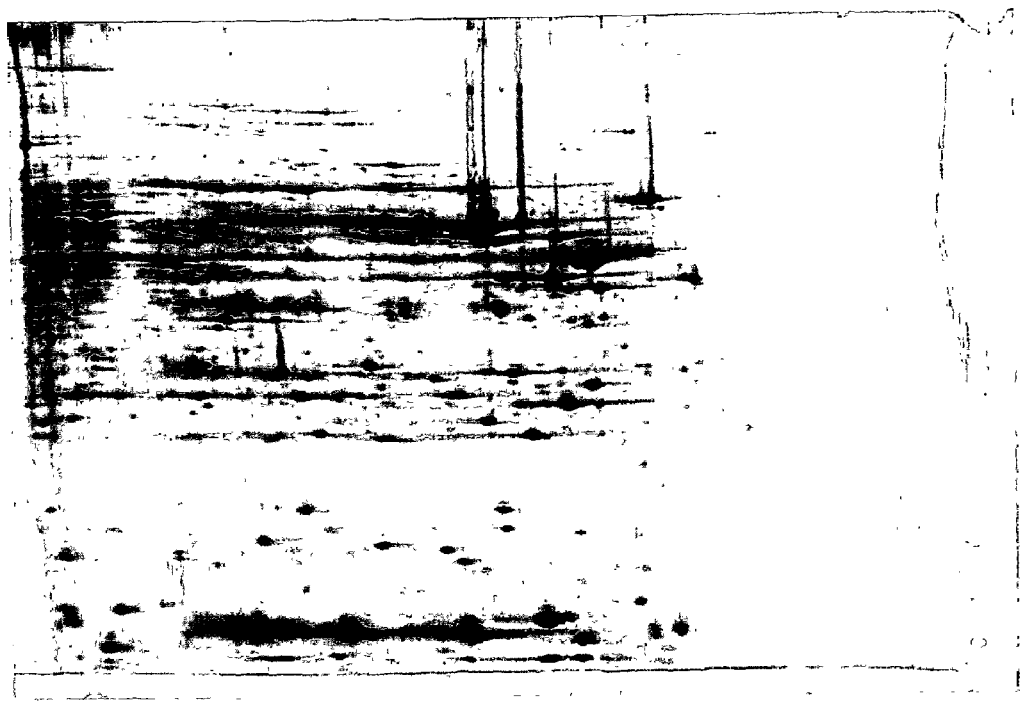
Figure 2d: 50 mM bis-(3-hydroxypropyl)-disulphide.

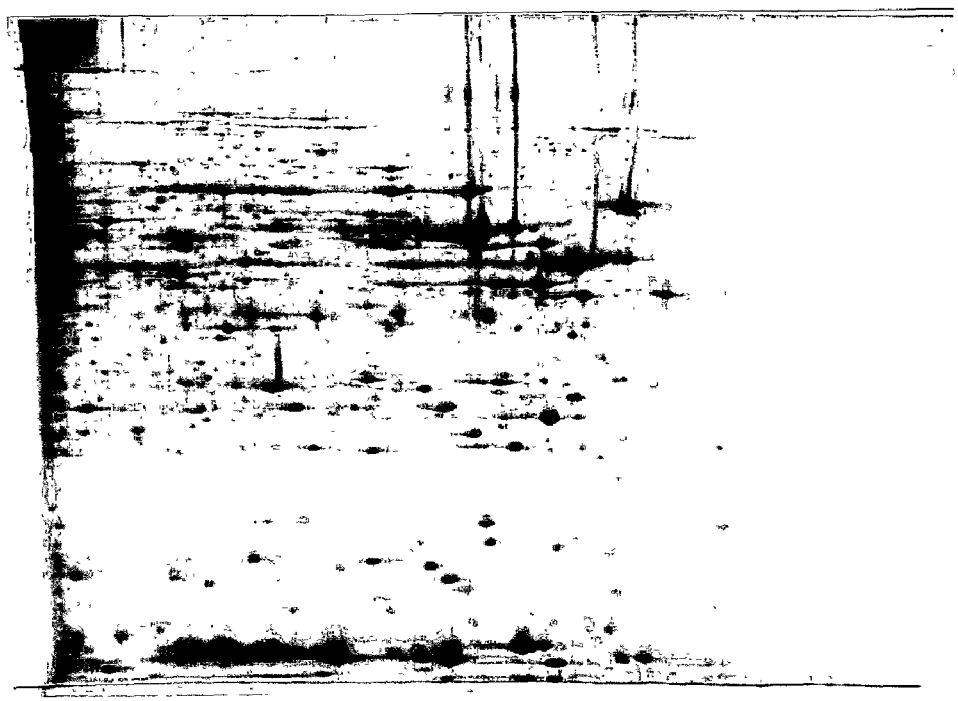
Figure 2e: 50 mM 3-((3-amino-3-oxy-propyl)dithio)- propane-amide.
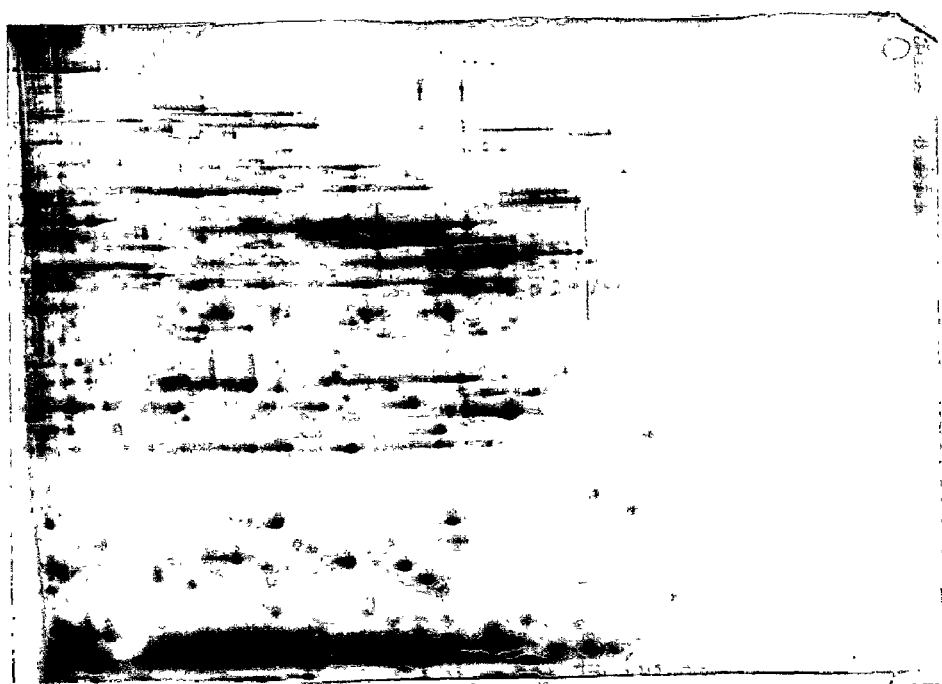
Figure 2f: 5 mM 2,2 dipyridyl-di-sulphide.

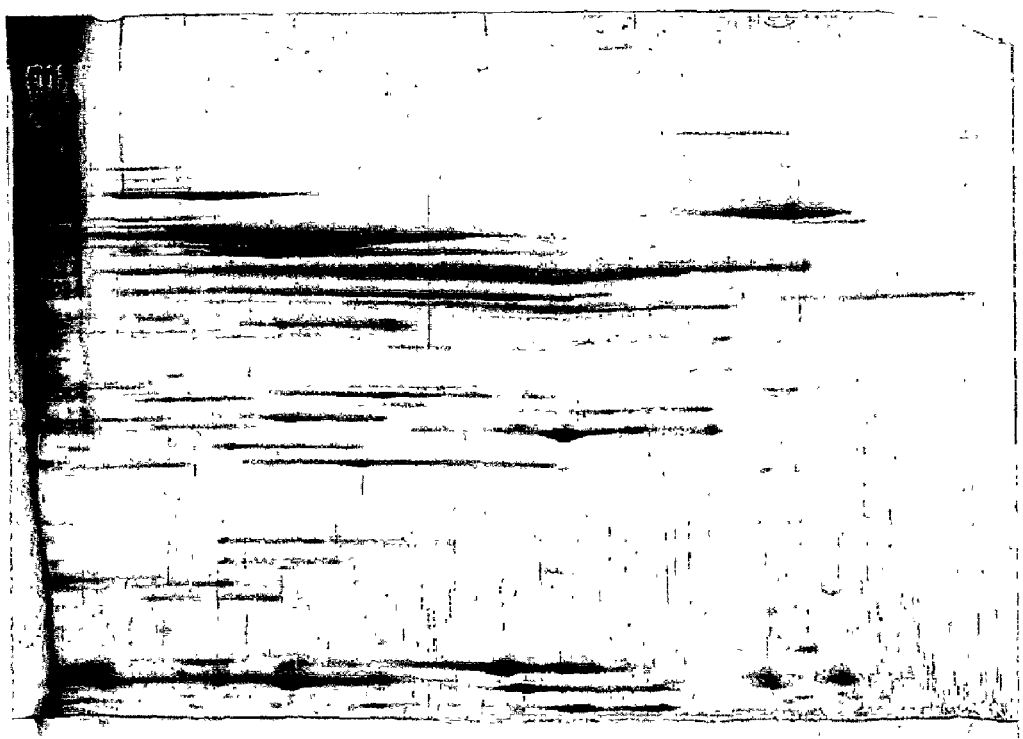
Figure 3a: 20 mM dithiothreitol
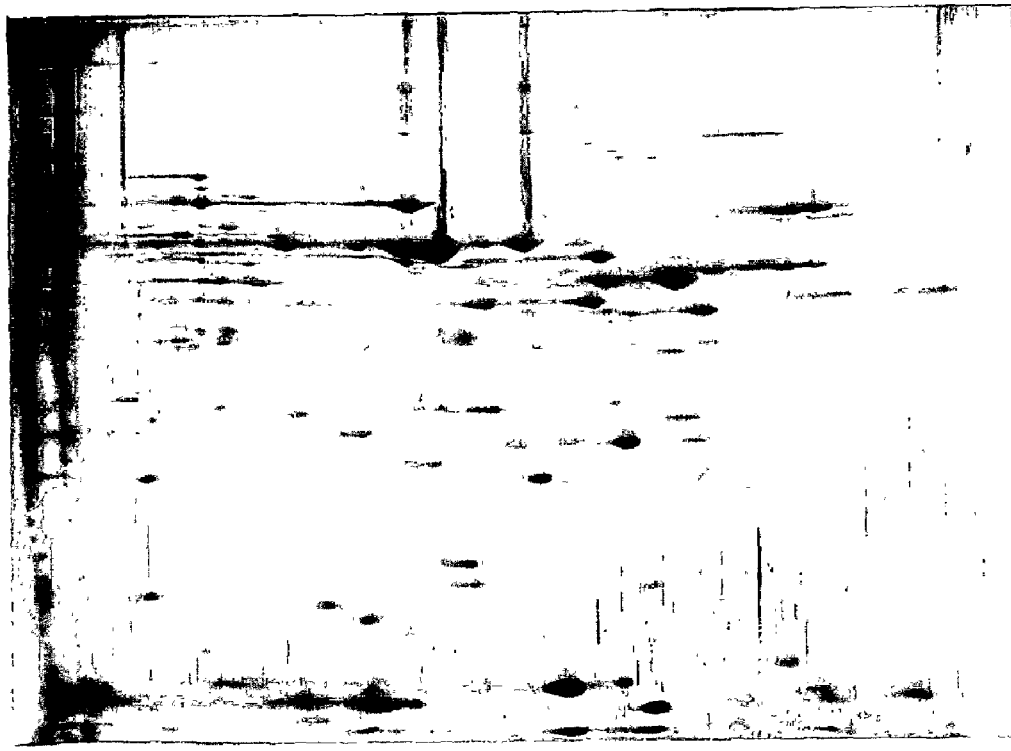
Figure 3b: 50 mM di-(2-hydroxyethyl)-disulfide

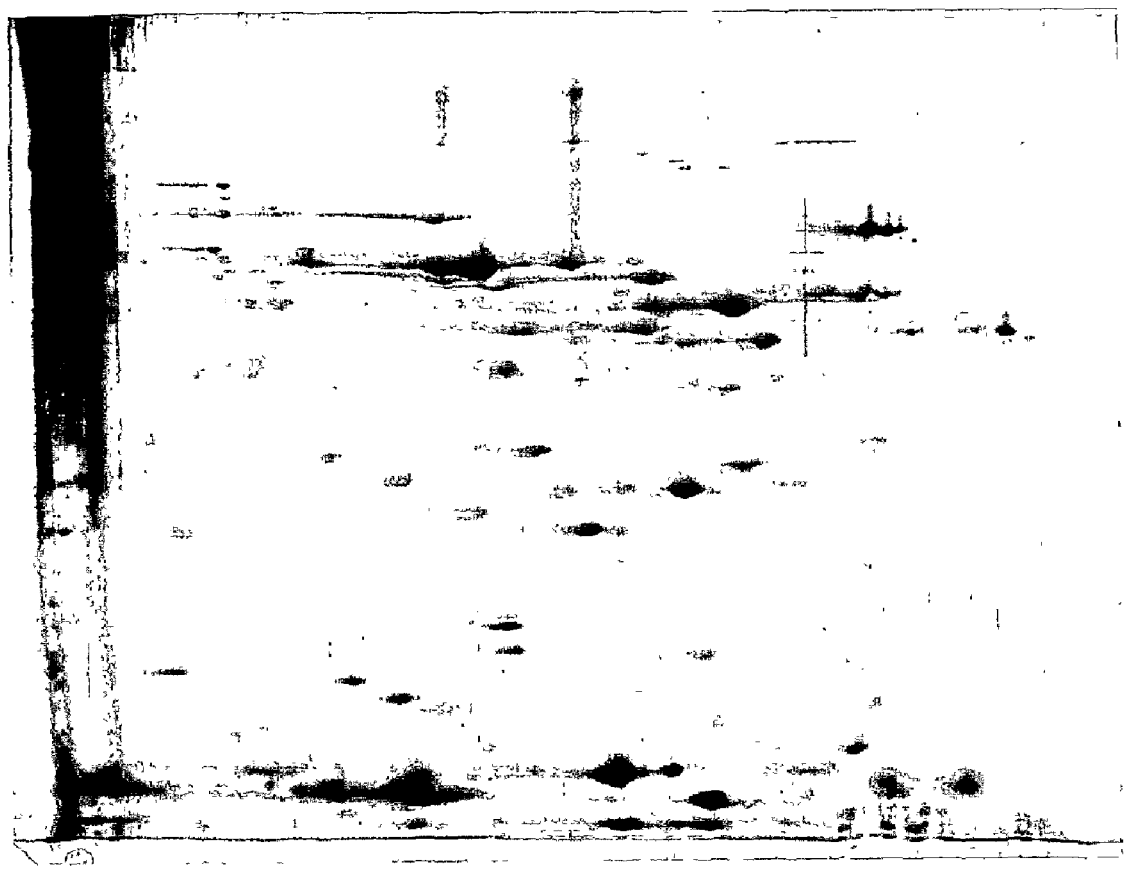
Figure 3c: 50 mM di-(3-hydroxypropyl)-disulfide

METHOD OF ELECTROPHORESIS

TECHNICAL FIELD

The present invention relates to the field of electrophoresis and more specifically to a method of separating protein and/or peptide components by electrophoresis. The invention also relates to a method of pre-treatment of a separation medium useful in the method according to the invention as well as to a kit useful for said pre-treatment.

BACKGROUND

The isolation of biomolecules, such as proteins and peptides, has become of an increased interest during the past years. Some biomolecules need to be isolated as a last step of a biotechnological method for the production thereof, for example in the preparation of protein-based pharmaceutical compounds. Similarly there is also a need to separate biomolecules for analytical purposes in order to be able to quantitate and identify the proteins and/or peptides present in a sample. Electrophoretic methods are commonly used in the separation step. A wide variety of methods are used for the detection and quantification of the separated proteins. For identification and characterisation of separated proteins MS methods are normally used as these methods are fast and require very small amounts of proteins and/or peptides.

In general terms, electrophoresis involves the movement of charged particles or ions in an electric field. The driving force for the electrophoretic transport of an ion or a particle is the product of the effective charge of the particle and the potential gradient, and the frictional resistance of the medium balances this force. The transport of a particle or ion is characterised by the electrophoretic mobility m, which is defined as the distance d travelled in the time t by the particle under the influence of the potential gradient E (m=d/tE). The electrophoretic mobility of proteins and peptides depend on the pH and the ionic strength of the medium in which the separation is done and of this reason the conductivity is given by some type of buffer components, which also control the pH and ionic strength of the medium. The systems generated in electrophoresis are gravitationally unstable and require some type of stabilisation. This has been achieved in variety of ways: by the use of density gradients generated of an electrophoretically immobile solute like glycerol; by performing the separation in capillaries, the capillary'space generated between two glass plates or in any other space of capillary dimensions generated on a chip; by doing the separation in paper or cellulose powder; by using a variety of gel-forming substances like starch, agarose or polyacrylamide. Gels like starch and acrylamide, but also linear polymers present in the liquid media in capillary geometry's, decrease the electrophoretic mobilities of proteins and peptides, and reinforce the dependence of the electrophoretic mobilities on the molecular weights of the proteins and/or peptides through the 'sieving' effect introduced by the polymer chains present in the media. It is common to include components in the separation medium that improve the solubility of the proteins and peptides to be separated. Examples of components used are well-known uncharged detergents like Triton and 3-[(3-Cholamidopropyl)dimethylammonio]-1-propanesulphonate (CHAPS), but also urea is a commonly used additive.

Based on how the pH and ionic strength is established along the separation distance, basically three different types of electrophoretic methods can be distinguished: The first type is zone electrophoresis, in which separation takes place in a medium of constant pH and ionic strength established with a conventional low molecular weight buffer present in the medium during the separation. In zone electrophoresis the sample is applied either at the cathodic or anodic end of the separation medium. To start the electrophoresis from a sample zone with a narrow width is in zone electrophoresis essential. A sharp narrow starting zone can be generated either by using the retardation resulting when the sample components enter a sieving media, with the aid of discontinuous buffer system or a combination of these two means. If the sample components to be separated are anions applied cathodic, the gel buffer in a discontinuous system will contain a buffering base and an anion with high electrophoretic mobility at the pH given by the gel buffer. Examples of commonly used anions are chloride, sulphate or acetate. The buffer in the cathodic electrode chamber normally contains the same weak base as the gel buffer and a partially negatively charged compound, which should have a lower electrophoretic mobility than the mobility of the sample components in the electrode chamber and/or in the eventual stacking gel at the pH generated in this gel and with the sieving effects of the gel taken into account. Examples of compounds used for the latter purpose are week acids as borate or amphoteric substances like glycine, tricine, alanine or HEPES titrated to pH values higher than the pI value of the compound. As a consequence of the arrangement, the sample components will be concentrated (stacked) into a narrow sharp zone localised at the boundary between the high mobility gel buffer anion for example chloride, and the low mobility anionic compound, for example glycine, originating from the electrode chamber. When this zone enter the separation gel the combined effects of an increased retardation of the sample components in the gel, and the increase of the mobility of the low mobility compound due to a pH shift, will result in that the electrophoretic mobility of the sample components become lower than the mobility of the anionic compound originating from the cathodic electrode chamber.

Sodium dodecyl sulphate (SDS)-electrophoresis is a variant of zone electrophoresis, which separates polypeptides according to their molecular weight. The SDS masks the charge of the proteins themselves and the formed anionic complexes have in free solution approximately identical electrophoretic mobilities independent of the size of the polypeptide. The molecular weight dependence is generated with the use of a sieving media, polyacrylamide gel is the media most commonly used for the purpose. A common and advantageous approach in connection with SDS electrophoresis is to utilise gradient gels containing varying concentrations of polyacrylamide where the a polyacrylamide concentration increase in the transport direction of the SDS-protein complexes from the sample application point towards the cathode. The mobilities of the protein will steadily decrease during the transport through the gel as a result of the variation of the sieving effect. SDS-protein complexes will remain stacked and move in narrow sharp zone localised at the boundary between the zone containing the gel buffer anion and the separation zone as long as the SDS-protein complex has a mobility higher than the weak acid present in the separation zone. As a consequence complexes corresponding to high molecular weight will destack already at low polyacrylamide concentration in an early state of the experiment. Low molecular weight complexes will remain stacked to close to the end of the experiment.

In zone electrophoresis the most common ways to establish the convectional stabilisation needed is either to use systems with capillary dimensions or to use some kind of gel. There exist a large variety of commercially available gels intended for different zone electrophoretic applications and normally designed to be used with a specific instrument. Most commonly, these gels are wet, ready to use, containing the buffer components and all other substances required for the specific application. However, dry gels are also available, which then are rehydrated prior to use in solutions containing the suitable components required for the use.

The second type of the electrophoretic methods is iso-electric focusing (IEF), in which separation take place in a stationary pH gradient that occupies the whole separation distance and is arranged so that the pH in the gradient increases from anode towards the cathode. While other alternatives also exist, the pH gradients required in isoelectric focusing are in practice generated in two different ways:

(a) with the aid of a solution of carrier ampholytes. With carrier ampholytes is understood a mixture, which contains a very large number of different amphoteric molecules. The demand on these amphoteric molecules are that each one should comprise a number of charged or chargeable groups resulting in a good buffer capacity at the isoelectric point of the amphoteric molecule and contribute with the conductivity required. The isoelectric points of the molecules in the ampholyte span a range of values, with a sufficient number of different isoelectric points among the molecules in the mixture to produce essentially a continuum of values of the isoelectric points. Thus, when a container is filled with a solution of a carrier ampholyte and a voltage is applied across the solution with an acid as the anolyte and a base as the catholyte, the individual ampholyte molecules arrange themselves in order of increasing isoelectric point from anode towards the cathode. A variety of synthetic carrier ampholytes are commercially available, such as Pharmalyte™, and Ampholine™ (all from Amersham Biosciences, Uppsala, Sweden). Carrier ampholyte generated gradients are not truly stationary, but show a slow drift and change of shape with time.

(b) with an immobilised pH gradient in which case the charged or chargeable groups generating the pH gradient is bound either to the wall of a capillary system or to the matrix when some kind of gel is used to get convection stabilisation. The immobilised charged or chargeable groups used are normally a limited number of carboxylic groups or amino groups with different pK-values distributed within or close to the pH gradient, which is to be generated. The concentration of the charged or chargeable groups is varied along the separation distance in a manner causing the pH at which the wall or the gel matrix has a zero net charge to increase from the anode to the cathode. A commercially available example of a system for generation of immobilised pH gradients is the Immobiline II system™ (Amersham Biosciences, Uppsala, Sweden), wherein a pH gradient covalently attached to a polyacrylamide gel is formed. Immobilised pH gradients are truly stationary and today they are normally used together with carrier ampholytes. In this combination the immobilised gradient determine the resulting pH gradient, while the carrier ampholytes contribute with conductivity.

The width of application zone is not critical in isoelectric focusing. In principal the sample can be mixed in to the separation medium and at the start of the separations be present all along the separation distance, but for analytical applications the sample is normally applied close to either the anode or the cathode. To provide the convectional stabilisation, capillaries and different types of gels are used also in isoelectric focusing . Examples of wet gels ready to use are Ampholine PAGplate™ gels, which exist for a number of pH ranges pH3.5–9.5, pH 4.0–6.5, pH 5.5–8.5 and pH 4.0–5.0. Examples of dry gels are Clen Gel IEF™ and Immobiline Dry Plate™ gels. A special variant of the latter type is the Immobiline DryStrip™ gels, which are designed to be used as first dimension in two-dimensional electrophoresis.

Besides that isoelectric focusing is used together with the convectional stabilisation means described as generally useful in connection with electrophoretic separation methods, it can also be used in chamber equipments. This type of equipment contains a number of compartments separated by membranes, which allow electrophoretic transport of carrier ampholytes and proteins between the chambers, but block the flow of liquid. A commercially available equipment of this type is the Iso-Prime™ (Amersham Biosciences, Uppsala, Sweden). The membranes used could either be uncharged or alternatively contain an immobilised pH. If the latter is the case, the immobilised pH will differ between the membranes and increase from the anode towards the cathode. Isoelectric focusing in chamber equipment has been used as prefractionation tool prior to 2-D electrophoresis, but also as mean for the purification of specific proteins.

The third type of the electrophoretic methods is isotachophoresis, in which the separation takes place in a region of varying pH and/or ionic strength. This region normally occupies a fraction of the total separation distance and is transported in the electric field during the separation. The mobilities of the proteins and/or peptides to be separated varies in the region in a manner, which makes them focus at different positions within the region where their respective transport velocity agrees with the velocity with which the gradient is transported. The pH variation could either be step-wise, generated with a limited number of compounds or alternatively it could be a continuous gradient generated with carrier ampholytes. An important application which fall in the latter category is non-equilibrium pH gradient electrophoresis (NEPHGE), which represents an alternative to IEF for separation of basic proteins in the first dimension of 2-D electrophoresis.

After an electrophoretic separation there is frequently a need to identify and characterise separated proteins and/or peptides, something normally done with mass spectrometric techniques. Especially SDS electrophoresis, as independent method or as second dimension in 2-D electrophoresis, is commonly combined with a subsequent identification and characterisation with MS. The normally procedure in this context is to cut out a gel plug containing a protein to be identified. Wash out eventual stain and other components present in the gel plug, which might disturb subsequent steps. Dry the gel plug down and then rehydrate the plug in a buffered trypsin containing solution. Generated peptide fragments is then extracted, resulting solution concentrated, applied and dried down on a MALDI target together with the matrix required for energy absorption at the wave length of the used laser. Identification from the generated peptide mass fingerprint is done by a search and comparison in a protein sequence database. Alternatively generated peptides can be analysed with ESI-MS or with MS/MS techniques in order to get amino acid sequence information as well as information on post-translational modifications.

In nature the sulphur containing side-chain of cysteines appear either as thiol groups, as disulphides connecting two cysteines or in a variety of other bonds, like the S-heme bonds or the iron-sulphur bonds found in many proteins involved in the respiratory chain. In the reducing environment existing in the cytosol, cysteinyl groups are normally present as thiol groups, while secreted or cell surface proteins often contain inter- and/or intra-chain disulphide bonds. The role of these disulphide bonds is to stabilise the three dimensional structure of proteins and also to keep the amino acid chains generating a protein or peptide together. Prior to an electrophoretic separation, it is common to reduce all inter- and intra-chain disulphide bonds present in the sample components to thiol groups. Whether the thiol groups are present originally, or generated in a reduction step, they very frequently create problems in electrophoretic separation methods, when the separation takes place at neutral or basic pH values. This is due to the high reactivity of thiol groups in this pH range and the fact that the reactions involved influence the behaviour of the proteins or peptides in the electrophoretic separations. The effect of the reaction of thiol groups is most pronounced in isoelectric focusing and becomes very conspicuous in 2D electrophoresis, a technique normally used to separate very large number of proteins. In 2-D electrophoresis as routinely performed today, the first dimension is usually an isoelectric focusing based on charge and the second dimension is a size-based sodium dodecyl sulphate (SDS) step. The first dimension focusing is conventionally performed in a polyacrylamide gel in the presence of a reducing agent, the function of which is to prevent thiol groups of sample proteins to oxidise or otherwise react during the focusing. Two commonly used reducing agents are dithiothreitol (DTT) and dithioerythritol (DTE), which are weak acids having pKa's of 8.3 and 9.0, respectively. Accordingly, both DTT and DTE are negatively charged at high pH values. Thus, during focusing in a gel that comprises a pH gradient, these substances will be transported away from the basic part of the gradient to be accumulated in a pH region of about 7–7.5. Thus, at basic pH values (pH higher than or equal to about 7) sample proteins' thiol groups will not be protected at all by the reducing agent. As the thiol groups are charged in this pH region, reaction of thiol groups will change the isoelectric point of the protein or peptide. If the conditions used result in a fast transport of proteins to the isoelectric point and the reaction rate for the consumption of thiol groups is comparatively slow, the observable result of a 2-D electrophoretic experiment is that a protein containing n thiol groups will appear in up to (n+1) protein spots in the resulting 2-D map, were these spots are connected with a faint streak. This kind of result is normally achievable only when anodic sample application is used, the separation distances are short and the pH gradient is steep. The need for anodic application is connected with that the reaction of thiol compounds is pH dependent and that cathodic application results in a fast formation of —S—S— bridges between molecules and generation of large protein aggregates. If high resolution is required, larger separation distances and flatter pH gradients have to be used, which decrease the rate with which proteins are transported. This intensify the streaking and with increasing separation distances and decreasing slope of the pH gradient the connected spots will gradually be converted to continuous streaks. The appearance of artifactual protein spots and/or streaks complicates or even prevents any accurate interpretation of the results.

Furthermore, the problems described for isoelectric focusing will appear in all kinds of charge-dependent electrophoretic separations performed at pH values higher than 7 as soon as the separation medium contains components which can react with the cysteinyl groups. It has long been considered a problem that residual unreacted acrylamide can form covalent adducts to proteins in conventional zone electrophoresis. Traces of remaining catalyst can similarly be expected to react with proteins and in all type of separations made in equipments where the separation media is in contact with air, oxidation of cysteinyl groups is expected. Urea added to get an improved protein solubility is another chemical which when present can react with thiol groups. As zone electrophoretic and isotachophoretic separations normally take much shorter time than isoelectric focusing, the heavy streaking that can appear with the latter technique is not normally noted. The problem observed is instead that each thiol containing proteins will appear as a number of bands, where the number of bands and the relative intensity of the bands will vary between experiments depending on the degree of oxidation of thiol groups.

In SDS electrophoresis the starting point is a sample containing proteins in which all cysteinyl groups present have been reduced to thiols. This is normally achieved by heating a protein containing sample to 95° for 3–5 minutes in a solution containing an excess of SDS and reducing agent, where the reducing agent normally used are either mercaptoethanol, DTT or DTE. SDS electrophoresis is normally performed in a polyacrylamide gel and most commonly with the well known buffer system according to Laemmli (Laemmli U.K (1970) Nature (London) 277, page 680). With this buffer system, the gel originally contains a Tris-chloride buffer of pH 8.7. The reduced sample containing SDS and a large excess of reducing agent is added at the cathodic end of the gel. The cathodic electrode buffer contains Tris, glycine and SDS. When the glycine and SDS enter the gel and substitute the chloride ions, a pH of approx. 9.5 will be established within the gel. At this pH mercaptoethanol as well as DTT and DTE have higher electrophoretic mobilities than glycine. As a consequence the reducing agent will immediately collect and concentrate in a narrow zone found between the zone containing the chloride ions originally present in the gel and the glycine zone in which the separation will take place. The passage of thiols through the gel will eliminate some compounds capable of reacting with cysteinyl groups. Especially when low molecular weight proteins and peptides are to be separated use of an acid with higher mobility than glycine can be required and tricine is for the purpose the most common choice. Also when storage stable polyacrylamide gels are used (pH of gel buffer <8) it is common to use acids with higher mobility than glycine. A number of different chemicals have been suggested and used in this context, examples besides tricine, are taurine and HEPES. Common to these compounds are, that in the pH range where they are used, their mobilities will be higher than the mobility of the thiol used as the reducing agent in the sample. Depending on the thiol used, some, or all the proteins and peptides to be separated, will move faster through the gel than the reducing agent. Irrespective if SDS-electrophoresis is run with glycine or a faster ion in the separation zone, the situation will be similar to the situation in isoelectric focusing at high pH values in the sense that there is no reducing agent present during the separation phase to protect the cysteinyl groups against reaction. The difference is that in SDS-electrophoresis the separation is independent of the charge of the protein. The described and known reactions of thiol groups in connection with SDS-electrophoresis are addition of acrylamide to form cysteinyl—S—β-propionamide and oxidation of thiol groups to form either inter- or intra-chain —S—S— bridges. Addition of one or a couple of acrylamide molecules to a protein marginally increases the mass of the protein, but has normally no detectable effect on the electrophoretic mobility of the protein-SDS complex in a polyacrylamide gel. Formation of inter-chain disulphide bridges, normally resulting in the generation of a dimer of a protein or peptide, result in drastic change in molecular weight and the electrophoretic mobility. Oxidation resulting in intra-chain disulphide bridges influences the shape of the SDS-protein complexes and result in small but detectable increase in the electrophoretic mobility. An oxidation product with deviating electrophoretic mobility will only be detected as a separated entity provided sufficient amount has been produced prior to that the product destacks. With a homogenous separation gel, which is a gel with constant acrylamide concentration, extra bands will only result if extensive oxidation takes place already in the stacking gel. Oxidation within the separation gel will only contribute with a diffuse background within the sample tracks. The situation becomes different in gradient gels especially for low molecular weight proteins containing at least two cysteines. In gradient gels it is normal to detect an extra artificial band or protein spot for this type of proteins. Even if the negative visible effects are less dramatic in SDS electrophoresis than in charge dependent electrophoretic separation methods, a solution to this problem is still desirable.

In connection with MS used for the identification and characterisation an initial step is digestion with trypsin. This step can not be run under reducing conditions as thiols like mercaptoethanol, DTT or DTE deactivate trypsin. None of the following steps involving extraction, concentration of generated peptides and drying down on the MALDI target together with matrix is done under reducing conditions. If reduced protein samples, where the cysteinyl groups are expected to be present as —SH, are digested with trypsin and used for identification with MALDI-TOF MS generated mass fingerprints, no masses corresponding to cystein containing peptides are found in the mass spectra. The probable reason is oxidation of the thiol resulting in —S—S— bridges, and maybe also a variety of other reactions, resulting in products with different masses negatively contributing to the background in the MALDI spectrum. For proteins separated with SDS electrophoresis prior to identification, cystein-containing peptides are detected as their —S-β-propionamide derivatives. The conversion of the thiol is incomplete and it seems as only the most reactive thiol groups are converted to propionamide derivatives to an extent, which allows the detection of the corresponding peptide in an MS spectrum. Clearly the degree of conversion will depend on the acrylamide concentration in the gel, which normally is high in home-cast gel but, as a result of the poisonous nature of acrylamide, kept low in commercial products. Method description exist for the alkylation of proteins with acrylamide prior to sequencing with conventional Edman degradation, which in principal should be possible to use either prior to the electrophoretic separation or between the electrophoretic separation and the MS identification. However, in reality, the reaction with acrylamide either is incomplete or alternatively ends up with the reaction of other nucleophils present in the proteins.

An approach frequently used in connection with 2-D electrophoresis is to use two equilibration steps between the first dimension and second dimension SDS electrophoresis. In the first step eventual —S—S— bridges formed are reduced with DTT and in second step available —SH groups are reacted with iodoacetamide. Although the conditions used allow detection of a number of cystein-containing peptides as acetamide adducts, this reaction is with the condition used also incomplete and cystein-containing peptides are missing in the resulting mass spectra As with acrylamide, use of higher iodoacetamide concentrations and/or longer reaction times result in the reaction of other nucleophilic groups present in the protein.

Several solutions to avoid the above-described problems have been proposed. For example, phosphines, such as tributylphosphine and tris-hydroxypropyl phosphine have been used to replace DTT and DTE as reducing agents. However, the tested phosphines have shown to entail problems due to low solubility, and also to result in various undesired side effects. As an alternative, alkylation of the thiol groups of proteins before electrophoresis has been suggested. However, this approach has been shown to result sometimes in a non-complete alkylation, and sometimes in undesired side effects. Moreover, it has been suggested to allow the reducing agent to continuously leak into the gel from the cathode side of the apparatus. However, this method requires very careful attention to avoid a too large amount of reducing agent, which may cause problems, while avoiding adding too small an amount, which will yield an unsatisfactory reduction.

The problem with the disappearance of thiol containing peptides in connection with MS is a problem not solely connected to the separation of proteins with electrophoretic methods and the modifications of thiols resulting during this separation. Independent of how the protein is purified the steps prior to MS identification is reduction of the proteins with MeSH, DTT or DTE followed by an alkylation step in which the commonly used alkylating agents are iodoacetic acid, iodoacetamide, vinylpyridine or acrylamide. After alkylation and prior to trypsin digestion a desalting step is normally done, after which the sample together with matrix is applied to a MALDI-target and dried down. The alkylation step is introduced to allow the detection of cystein containing peptides in the resulting mass spectra. As already discussed this type of alkylation reaction is not ideal for the purpose. Either the result is only a partial conversion of the thiol groups present in the sample, alternatively other nucleophilic groups present in the sample will react. In the former case peaks corresponding to some cysteinyl-containing peptides will be missing in the resulting mass spectrum, in the latter case artefactual peaks with non-predictable masses will appear in the mass spectra. Thus, there is a need of a reaction with better selectivity, which allow a complete or close to complete conversion of the thiol groups without causing any side reaction, will clearly be advantageous prior to identification and characterisation of proteins and peptides with mass spectrophotometric methods.

Accordingly, there is a need in this field of a method, which eliminates the negative effects of reactions of thiol groups on separations, especially methods performed with electrophoretic methods. Simultaneously there is need for a method or reaction, which allow efficient and close to complete conversion of all cysteinyl groups, present in a protein and/or peptide containing sample, to a defined form possible to detect and study with mass spectrometric methods, at the same time as modifications of other groups present are avoided or at least kept to a minimum.

SUMMARY OF THE INVENTION

One object of the present invention is to provide an electrophoretic method of separation of proteins and/or peptides, which results in more clearly interpreted results than the prior art methods. More specifically, the object is to provide a method of separating protein and/or peptide components of a sample, which method avoids or at least reduces any unclear results caused by the presence of thiol groups during the separation.

Another object of the present invention is to provide a method of separation as discussed above, wherein streaking of the resulting spots is avoided.

A specific object of the present invention is to provide a method of separating components as described above, which method avoids artefact spots and consequently improves reproducibility as compared to the prior art methods.

One or more of the objects above are achieved as defined by the appended claims. Further embodiments and advantages of the present invention will be explained in more detail below.

BRIEF DESCRIPTION OF THE DRAWINGS

FIG. 2a–f compare resulting 2-D maps with the first dimension focusing in IPG-strips pH 6–11 either with prior art methods (FIG. 2a and 2b) or containing illustrative disulphides according to the invention (FIG. 2c, d, e, f).

FIG. 3 a–c compare resulting maps with a long narrow range IPG-strip pH 7.5–9.5 as first dimension with prior art methods (FIG. 3a) and with strips rehydrated with disulphides (FIG. 3b and 3c).

FIG. 5a shows the result when the first dimension strip neither contains any reducing agent nor any disulphide, while

DEFINITIONS

Figure 1:
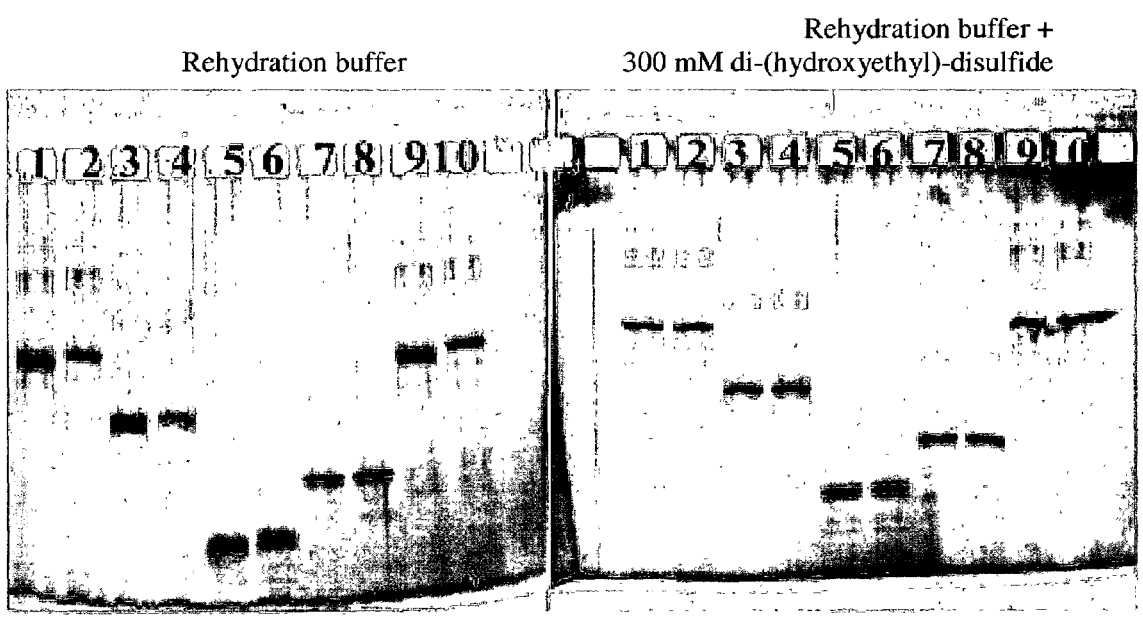
FIG. 1 compares the results of SDS-electrophoresis experiments run according to prior art methods with the method according to the invention.

In the present specification, the term "peptide" is understood to include both smaller peptides and larger polypeptides. Accordingly, the term "protein and/or peptide" as used herein includes any molecule comprised of a chain of amino acids, wherein the amino acids are covalently linked by peptide bonds.

The term "carrier ampholyte" refers to a complex mixture, which consist of multiple chemical substances that differ from each other by the nature and the number of basic and acidic groups. Therefore, each ampholyte species has its own isoelectric point. The term "capillaries" is understood to include any type of space with dimensions sufficiently narrow to create, in combination with the separation medium, the convectional stabilisation required for the accomplishment of an electrophoretic separation. Besides ordinary capillaries the term also includes for example the capillary space generated between two glass plates and different types of spaces possible to generate on a chip.

The terms "stacking gel" and "stacking zone" as used in the present specification means a gel or zone, which the sample components in zone electrophoretic separation passes prior to the entrance into the separation medium. During the passage of the stacking gel or zone the sample components are concentrated (stacked) into one narrow sharp zone from which the separation based on mobility differences can start when this zone enters the separation medium.

The term "mixed disulphides" means a disulphide in which one of the sulphur atoms originates from a cysteinyl group in a protein or peptide while the other originates from a disulphide added during the separation according to the present invention The term "intra chain disulphides" or "disulphide bridges" means disulphides generated from two cysteinyl groups belonging to the same amino acid chain, while "inter chain disulphides" or disulphide bridges refer to disulphides generated from cysteinyl groups belonging to different amino acid chains.

The term "reactive disulphide" means herein any disulphide that is capable of reacting chemically e.g. with thiol groups.

The term "chargeable groups" means herein such groups that through protolysis equilibria in relation to the used separation medium can give positive or negative net charges. "Chargeable groups" typically comprise one or more of the elements carbon (C), sulphur (S), phosphorous (P), boron (B) or nitrogen (N).

DETAILED DESCRIPTION OF THE PRESENT INVENTION

A first aspect of the present invention is a method of electrophoretic separation of one or more protein and/or peptide components of a sample, which method comprises to
(a) contact the sample with a convection stabilised separation medium;
(b) apply a voltage across said medium; and
(c) observe the results of the separation obtained by analysis of one or more sections of the separation medium;
wherein a disulphide-comprising compound is added in an amount sufficient to provide an excess of reactive disulphide groups to said components during the separation procedure. The observation according to step (c) can be any conventional method of evaluating the results obtained, such as a qualitative and/or quantitative analysis. In the present specification, the disulphide-comprising compound is sometimes simply denoted disulphide.

Thus, the thiol groups of the cysteine residues present in the sample are according to the present invention reacted to disulphides by addition of a sufficient amount of reactive disulphide groups to transform said thiol groups into mixed disulphide groups, where one sulphur atom represent a cysteinyl group, while the other sulphur originates from the added disulphide compound. The amount of added disulphide-comprising compound is easily determined by the skilled in this field depending on the sample to be treated and a brief assessment of the amount of SH-groups available for reaction therein. As is easily realised, for practical reasons, a large excess is preferred.

Thus, the present invention shows for the first time that a much improved electrophoretic separation result if the thiol groups of proteins are oxidised to mixed disulphides by the addition of a disulphide-comprising compound. As mentioned above, according to the prior art, attempts have been made to maintain the thiol groups by adding a reducing agent, to avoid any reactions thereof. Furthermore, acrylamide and iodoacetamide have been utilised to alkylate the thiol groups prior to the separation. However, these type of alkylation agents tend to also react with other nucleophilic groups present in a protein or peptide and the result is either incomplete conversion of the thiol groups or if larger amount of the alkylating agent is used, unwanted side reactions. The reaction of the thiol groups with disulphide according to the present invention is a much milder, highly specific reaction that allows all or essentially all of said thiol groups to be converted to mixed disulphides. If desired, the thiol groups of the protein and /or peptides can easily be regenerated after finished separation by reducing the separated components with either DTT or DTE. Alkylation with iodoacetamide or iodoacetamide represents an irreversible reaction, from which the thiol can not be regenerated.

Even though it is possible, and in the case of zone electrophoresis a necessity, to transform the thiol groups of the sample before it is subjected to the separation procedure, for best results, the addition of disulphide-comprising compound should be made in a way so that reactive disulphide groups are continuously accessible to the sample. As will be discussed in more detail below, in one embodiment, the disulphide-comprising compound is added to the separation medium and/or sample before step (a).

The electrophoresis according to the invention is run in accordance with well-known principles. Thus, the voltage and amperage applied, as well as the separation time required will depend on the method and the kind of separation medium used. In addition, a brief overview of the principles of various methods encompassed by the present invention is given in the section "Background" of the present specification.

Thus, in one embodiment, the separation medium comprises one or more surfaces or spaces of capillary dimensions. Capillaries can for example be present on chips. In another embodiment of the present method, the separation medium comprises a gel. The gel can for example be made of synthetic polymers, such as a polyacrylamide gel, or of native polysaccharides, such as an agarose gel. In a specific embodiment, the gel is treated with a liquid comprising a disulphide comprising compound before step (a).

The present electrophoretic separation can for example be a zone electrophoresis. Thus, in one embodiment of the method, one or more buffers are added to keep the conditions of pH and ionic strength essentially constant in the separation medium during the electrophoresis.

In one embodiment, the separation medium comprises an anionic or cationic surfactant. Typically this surfactant is dodecyl sulphate. The role of said charged surfactant is to mask the charge of the sample components to be separated. The surfactants have higher electrophoretic mobilities than the sample components to be separated. While they can be present in the separation medium at the start of the separation, this is not a necessity, as long as they enter the separation medium together with the sample and is present together with the sample components throughout the separation. To achieve this, the surfactant is one of the components in at least one of the electrode chambers. As the skilled person will realise, dodecyl sulphate as anionic substance has to be present in the cathodic electrode chamber, while if a cationic surfactant is used, it needs to be present in the anodic electrode chamber. In this embodiment the separation medium will also comprise some type of polymeric substance, such as polyacrylamide. The role of the polymeric substance is to make the electrophoretic mobilities of the sample components dependent on their respective size and geometry and in that way make the mobility connected to molecular weight.

In a specific embodiment, the sample is treated with a charged surfactant to mask the charge of the proteins and/or polypeptides therein before it is contacted with the separation medium and wherein the proteins and/or peptides are separated according to their molecular weight. In the case of SDS-electrophoresis the treatment with SDS is normally also connected to a reduction of the thiol groups present in the proteins and/or peptides. To be used in zone electrophoresis this type of samples need to be reacted with disulphide prior to that the proteins and/or peptides enter the separation medium. This can be performed either by adding a sufficient excess of disulphide to the sample to convert all the thiol groups in the sample to mixed disulphides prior to sample application alternatively the reduced sample solution can be added to a stacking gel or stacking zone, where the stacking gel or zone contains disulphide to an extent which result in a complete conversion of the thiol groups in the sample to mixed disulphide during the sample transport through the stacking gel or zone, but prior to the entrance of the proteins and peptides into the separation medium. A preferred alternative is to solubilise the sample in a solution which besides the detergent contains an excess of disulphide and a small catalytic amount of reducing agent.

The present method can also follow the principles of an isoelectric focusing method. Accordingly, in one embodiment, a stationary pH-gradient is formed by providing charged or chargeable groups along all or essentially all of the separation distance in the convection stabilised separation medium and the proteins and/or polypeptides are separated according to their isoelectric points. Examples of negatively chargeable groups are carbonic acid, sulphonic acid, boric acid, phosphonic acid, and phosphorous acid. Positively chargeable groups can e.g. be various amino groups or other chargeable nitrogen compounds.

In one embodiment, the charged or chargeable groups are non-mobile and affixed to or into a matrix. In a specific embodiment, the matrix is the separation medium. Most preferably the matrix is a polymer which will form a gel with the other components present in the separation medium. A commercially available example of such a system is the Immobiline II System™ (Amersham Biosciences, Uppsala, Sweden), wherein the charged and chargeable groups that generate the pH gradient during the separation are covalently attached to a polyacrylamide gel.

In one embodiment, as discussed above, isoelectric focusing can be performed using capillaries. In this embodiment the charge or chargeable groups that generate the pH gradient for the separation are bound to the walls of said capillary system.

In an alternative embodiment of the present method, the charged or chargeable groups are comprised in carrier ampholyte molecules. Thus, in this embodiment, the separation medium comprises carrier ampholytes. The respective isoelectric points of the molecules in the ampholyte span a range of values, with a sufficient number of different isoelectric points among the molecules in the mixture to produce essentially a continuum of values. Thus, when a container is filled with a solution of a carrier ampholyte and a voltage is applied across the solution with an acid as the anolyte and a base as the catholyte, the individual ampholyte molecules will arrange themselves in order of increasing isoelectric point along the direction of the voltage. The container can be any cell or vessel, such as a flat plate sandwich, a tube, or a capillary. In this embodiment the convection stabilisation can also be created by an uncharged gel generated with for example acrylamide or agarose.

Carrier ampholytes can be formed from synthetic substances or from naturally occurring materials. A variety of synthetic carrier ampholytes are commercially available, such as Pharmalyte™, and Ampholine™ (all from Amersham Biosciences, Uppsala, Sweden).

As described above, a pH gradient can be generated by buffering groups bound either to a polymeric structure present in separation medium, to the walls of a capillary system or to membranes separating chambers in that type of embodiment and without addition of carrier ampholytes to the separation medium. This is sometimes advantageous in micropreparative experiments as it eliminates the need after finished separation to purify the proteins from carrier ampholytes. The drawback with the use of only immobilised buffering groups is that the conductivity resulting during the separation become very low, which drastically increase the separation time required. As a consequence the use of immobilised groups are normally combined with addition of carrier ampholytes to the separation medium. In this embodiments the immobilised groups determine the pH gradient resulting in the separation, while the carrier ampholytes contribute with the conductivity required to keep the time required for the separation down.

In an alternative embodiment, the present method uses a container, which has been divided into separate chambers by membranes, thus allowing the components to be separated to pass across, but blocking liquid flow between the compartments during and after finished separation. This embodiment is advantageous in preparative work as separated pure proteins or protein fractions are easy to collect after finished separation and it also represents an advantageous prefractionation method prior to 2-D electrophoresis when narrow range pH gradients are used for the first dimension focusing. The charge or chargeable groups required for establishing of the different pH values could belong to carrier ampholyte molecules comprised in the separation medium alternatively the charged or chargeable groups could be bound to the membranes used to separate the chambers in the equipment. In the latter case the membrane can be comprised of polyacrylamide gel polymerised on a suitable support for example a glass fibre filter.

Thus, in a specific embodiment, the present method is performed in an apparatus comprising at least two chambers separated from each other by membrane(s).

In summary, isoelectric focusing electrophoresis according to the invention can in principle be performed in cells of all forms and shapes, notably capillaries, slabs, and tubes. In capillaries the separation medium is not necessarily a gel, but is in fact most often the buffer solution itself. However, the most frequently used for analytical purposes are gels bond to a plastic backing. Gel strips is the preferred configuration in two-dimensional electrophoresis. For example, IPG™ strips are commercially available dry for the pH intervals 3–10; 3–7; 4–7; 6–11; 6–9; 3,5–4.,5; 4–5; 4.5–5.5; 5–6; 5.5–6.7; 6.2–8.2; and 7.5–9.5.

Sample application in isoelectric focusing electrophoresis according to the invention can be done anywhere along the separation distance and contrary to the situation in zone electrophoresis, the width of the sample zone from which the separation starts is not a critical issue. As discussed earlier isoelectric focusing of reduced thiol containing samples in basic gradients with prior art methods require the use of a sample application point close to the anode to give reasonable result. Also when isoelectric focusing is done according to the invention sample application close to the anode is the preferred approach, when pH gradients extending to pH-values higher than 7 is used, as this approach is insensitive to the presence of reducing agents in the sample. Reduced samples containing concentration normally used in connection with sample solubilisation give high quality separations and the results are of the same quality as with sample in which the thiol groups have been oxidised to mixed disulphides prior to sample application. As a result of the elimination of the thiol groups of protein and/or peptides achieved with the present invention, and contrary to the situation with the prior art methods, application close to the cathode can be used also with basic pH gradients and in an alternative embodiment the sample can be mixed in the rehydration solution and accordingly added throughout the separation medium before the focusing procedure is initiated. It has been found that with the two latter application methods the content of reducing agent in the sample has a marked influence on the quality of the resulting separation in a pH region centred somewhere around pH 7–8. For example, bis-(2-hydroxyethyl)disulphide was added to a reduced sample, wherein the reacted sample had been included in the rehydration solution, in which case streaking was avoided in basic IPG strips of pH 9–12. However, less advantageous results were obtained at pH 7–8, which can be explained by a reduction of the disulphide by the reducing agent and a generation of mercaptoethanol transported to this specific pH interval. Clearly the specific region in which the disturbance will appear will obviously depend on the pK-value of the thiol-containing compound generated in the reduction of the disulphide. Accordingly, to avoid the undesired streaking the sample should contain a minimum amount of reducing agent. In techniques were the sample solubilisation is connected to reduction a minimum amount of reducing should could be used to solubilise the sample. An alternative preferred approach is to convert the thiol groups of the proteins and peptides already in connection with the sample solubilisation, i.e. to make the sample solubilisation in a solution containing an excess of disulphide and small catalytic amount of a reducing agent.

Another alternative is that the present electrophoretic separation follows the principles of isotachophoresis. Thus, in one embodiment, a gradient of pH and/or ionic strength is formed by providing charged or chargeable groups along a part of the separation distance in the convection stabilised separation medium and transported in the electric field and wherein the proteins and/or polypeptides are separated according to their respective transport velocities.

As regards the separation media and generation of pH gradients, basically the same known principles as discussed above in relation to isoelectric focusing will apply. In an advantageous embodiment, the separation medium comprises carrier ampholytes. An important isotachophoretic variant is NEPGE (non-equilibrium pH gradient gel electrophoresis), which during many years was the dominating method for the first dimension separation of basic proteins in 2-D electrophoresis.

As regards the variable ionic strength, the applied principles are well-known to the skilled person in this field.

As is well known, in isotachophores sample application is limited to be done either close to the anode or close to the cathode. Otherwise the same principals and rules are valid as for isoelectric focusing Thus, the present method can follow the principles of any method selected from the group that consists of zone electrophoresis, isoelectric focusing and isotachophoresis.

As mentioned above, the excess of reactive disulphide can be provided by adding a disulphide-comprising compound to the separation medium before the sample is added. In the cases where the separation media comprises a liquid constrained to capillary dimension the disulphide can be solubilised in this liquid prior to its use. In the cases were the separation medium comprises a gel the disulphide can be included together with other components like urea detergent and/or buffering compounds required for the separation in the solution used for the generation of the gel. Typically it could be added to a melted agarose solution prior to the pouring of the gel. Contrary to the situation with thiols it is also possible to include disulphides, provided that the used disulphide not contain other interfering with the reaction, in solutions used for radical polymerisation. Polyacrylamide gels containing disulphides can thus be produced and this is an advantage over prior art methods since acrylamide can not be polymerised in the presence of thiols like DTT or mercaptoethanol. Since many commercial gels are sold in dried state, the addition of disulphide can also be conveniently accomplished by soaking such a previously dried gel in a rehydration solution supplemented with one or more suitable disulphide-comprising compounds. The other components of such rehydration solutions will be discussed in more detail below.

In the most advantageous embodiment of the present method, adding a disulphide-comprising compound, which is not charged in the pH interval where the separation is performed, provides the disulphide groups. Alternatively, it may be acceptable that the disulphide-comprising compound has a minimal negative net charge in said interval, as long as the charge does not impair the function of the gradient. Accordingly, one advantage of the present invention is that contrary to the previously used reduction agents, the disulphide-comprising compound used according to the invention will not be transported by the pH gradient. Thus, the protein's thiol groups will be protected as disulphides at all pH values, resulting in clear and reproducible maps. In this context, it is noted that compared to maps resulting from conventional isoelectric focusing, where the proteins' cysteine groups are present as thiols, the spots that appear as a result of the present method will appear at a slightly higher pI, while the molecular weight is essentially the same or slightly increased, since as the skilled person in this field will realise, the additional molecular weight will have a greater relative impact on a small peptide than on a large protein. In total, a protein map obtained according to the present method will also exhibit a reduced number of spots, since the previously appearing side reactions are now avoided or at least essentially reduced.

Thus, in one embodiment, adding a disulphide-comprising compound the pKa of which is near the pKa of the thiol group of cysteine provides the disulphide formations. In another embodiment, the pKa of the disulphide-comprising compound is above the pKa of the thiol group of cysteine.

The general mechanism underlying the present invention can e.g. be illustrated by the following equilibria:

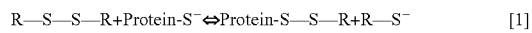

wherein R is any suitable alkyl, such as a hydroxyalkyl, an amide, such as an alkanamide, an aryl such as phenyl, a heterocycle, such as pyridyl, where R can preferably be substituted with a group that increases the solubility; and wherein P is a protein or a peptide.

$$K_1 = \frac{[PSSR][RS^-]}{[RSSR][PS^-]} \quad [4]$$

$$\frac{PSSR}{PS} = K_1 \frac{RSSR}{RS^-} \quad [5]$$

$$\frac{RSH}{RS^-} K_1 = H^+ \quad [6]$$

$$RS^- = K_3 \frac{RSH}{H^+} \quad [7]$$

$$PS^- = K_2 \frac{PSH}{H^+} \quad [8]$$

$$\frac{PSSR}{[PSH]} = \frac{K_1 K_2}{K_3} \frac{[RSSR]}{[RSH]} \quad [9]$$

$$K_1 K_2 >> K_3 \quad [10]$$

When the overall equilibrium constant $K_3$ is divided into equilibrium constant $K_1$ and $K_2$ for each of the component reactions, both of the new values are found to be near to unity. A general conclusion is that the mixed disulphide is an important product.

The above-discussed thiol-disulphide exchange is a special form of alkylation, namely an s-alkylation. This reaction is easily reversible and the reaction is a nucleophilic two-step in which a mixed disulphide is formed as an intermediate.

In one embodiment, to stabilise this intermediate and to convert it to the major product, RSH must be an weak acid or the thiol must be quantitatively transformed into a mixed reactive disulphide concomitantly with formation of equimolar amounts of thione, scheme 1.

Scheme 1
Thiol-disulphides exchange reaction with 2-thiopyridyl.

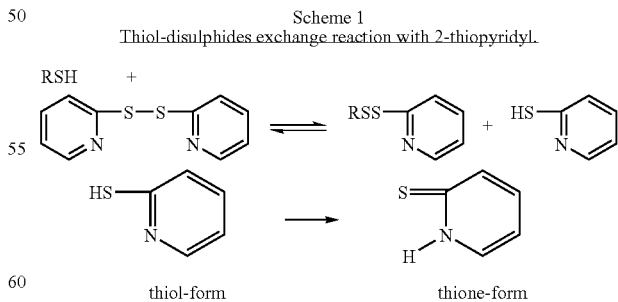

The thione form facilitates the disruption of the S—S linkage because the liberated thiol is stabilised by resonance in the thione form explaining the high reactivity of pyridine disulphide. The reaction with thiopyridyl compounds will proceed at pH-values where thiol-disulphides exchanges are slow or non-existent. In fact, thiol-disulphide exchange with pyridyl disulphides can be carried out at pH-values in the range 1–9.

Thus, in one embodiment, the disulphide groups are provided by adding a disulphide-comprising compound that the pKa of which is near or above the thiol group of cysteine.

As can be seen from these formulas the equilibrium [1] will be shifted towards the right side with the protein thiol groups in the form Protein-S—S—R provided that the concentration of the disulphide R—S—S—R can be kept high and the concentration of the thiol in its deprotonated form low. As also shown in formula [1], it is the deprotonated form of the thiol groups that participates in the reaction. As a consequence the value of the dissociation constants more precisely the ratio of the dissociation constants for reactions [2] and [3] will directly influence the Protein-S—S—R/Protein-S⁻-ratio resulting from the equilibrium [1].

To simplify the situation the given reaction formulas indicate the use of a symmetric disulphide. In reality an asymmetric disulphide could just as well have been used, and is therefore encompassed within the scope of the present invention. As will be described below, this can under certain circumstances also be favourable.

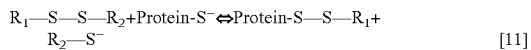  [11]

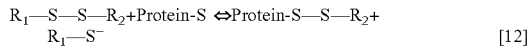  [12]

  [13]

  [14]

  [15]

Thus, by adding a disulphide-comprising compound having the general formula R—S—S—R, the equilibrium is shifted to the left, and an increased proportion of the protein will be present in disulphide form. Accordingly, the problems associated with the prior art, which were described above as streaking of spots due to a change of the protein's pH when its thiol groups react, can be substantially reduced or even eliminated according to the present invention. Likewise, the other previously observed problem with artefact spots caused by reaction of thiol groups is also reduced or even eliminated.

In the case where a protein-SH group reacts with a simple disulphide, only a mixed disulphide is usually possible. This is because, unless the protein has a second nearby SH group as well, formation of an unmixed one would require a specific and thermodynamically unfavourable alignment before dimerization.

The rate of a thiol-disulphide exchange reaction is pH-dependent because the thiol participates as RS⁻. Acidification therefore "freezes" the products.

Disulphide-disulphide Exchange:

Thiol-disulphide exchange enables disulphide-disulphide exchange to occur if a catalytic amount of a thiol is present. The reaction is a general one. Protein-S—S groups, for instance, give mixed disulphides on reaction with non-protein disulphides. The sequence, with RSH as the catalytic thiol, is as follows:

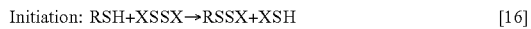  [16]

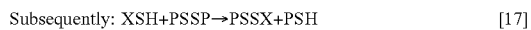  [17]

  [18]

The thiol-catalysed disulphide-disulphide exchange, as expected, becomes faster as the pH is increased. This is in contrast to the direct disulphide exchange that is found only in strong acid and is inhibited by thiols.

In a specific embodiment, the disulphide groups are provided by adding a disulphide-comprising compound selected from the group that consists of bis-(2-hydroxyethyl) disulphide; bis-(2-hydroxypropyl) disulphide; 3,3-dipropionamidedisulphide and 2,2'-dipyridyl disulphide.

Accordingly, a second aspect of the present invention is the use of a solution comprising a reactive disulphide-comprising compound to pretreat, such as to rehydrate, a gel for electrophoresis. In one embodiment, such a solution contains one or more of the disulphide-comprising compounds discussed above together with further components that are commonly present in a rehydration solution, such as urea, detergent, such as CHAPS, carrier ampholytes etc. Which other components to use and their concentrations in the rehydration solution depend on the electrophoretic technique and the specific application involved. For SDS-electrophoresis the used solution normally only contains the buffer components required, typical a Tris/HCl or a Tris acetate buffer with a pH value in the region 6.5–9, and optionally a small amount, 0.1–0.2%(w/v) SDS. For isoelectric focusing an illustrative composition of a conventional rehydration solution is 8M urea, 0.5–2% of carrier ampholyte, a non-ionic or amphoteric detergent and, when used in prior art technique, as well a reducing agent such as DTT, DTE or tributyl phosphine.

For a rehydration according to the present invention, the reducing agent should be substituted with disulphide-comprising compound(s) according to the invention and if sample application is done by including the sample in the rehydration solution step, the amount of reducing agent should be kept close to the minimum required for the preceding sample solubilisation step. DTT, DTE or TBP will react with the disulphide comprising compound in the rehydration solution to generate the corresponding thiol, which will shift the equilibrium of reaction [1] towards the right and result in an decrease of the Protein-S—S—R/Protein-SH -ratio. The concentration of reactive disulphide comprising compound required will thus not only depend on the ratio of the equilibrium constants for reaction 2 and 3, but also on the reducing activity present in the gel or rehydration solution and in the specific case of isoelectric focusing on the amount of reducing activity added with the sample. Also when a sample is applied cathodic to an isoelectric focusing gel, thiol, generated from the reaction of the disulphide comprising compound with any reducing agent present, will enter the gel and contribute negatively to the Protein-S—S—R/Protein-SH ratio. When reduced sample are applied anodic to a focusing gel the cysteinyl groups in the proteins entering the gel will convert the disulphide added with rehydration solution to the corresponding thiol and when large protein loads are used this can also significantly influence the Protein-S—S—R/Protein-SH ratio. The concentration of disulphide comprising compound required to eliminate streaks and/or artifactual spots, varies within a wide concentration range and depend on the amount of reducing added to the strip with the sample and the concentration distribution resulting during focusing as well as on the equilibrium constants valid for the reactions [1]–[3], which then depend on the used disulphide comprising compound. While concentrations of the order of 2–5 mM of dipyridyldisulphide have been shown to give good results with anodic sample application in connection with isoelectric focusing and this type of concentrations can be expected to improve the resulting focusing pattern also when other disulphides are used, it is in most cases favourable to use appreciably higher concentrations of disulphide falling in the region 20–500 mM. Based on the chemical equilibria involved highest possible should be the most favourable choice, and provided that the used disulphide not in any other way negatively influences the prerequisites for the electophoretic separation the solubility of each compound in the solution used will set the upper concentration limit possible to use.

Another aspect of this invention is a solution for solubilisation of proteins and/or peptides to be used as samples in an electrophoretic separation according to the invention. Said solution is intended to substitute the solutions conventionally used in techniques where reduced proteins/and/or peptides are used as sample. Examples of techniques of this type are SDS-electrophoresis and isoelectric focusing as in 2-D electrophoresis prior to a second dimension SDS-electrophoresis. With the prior art techniques the solutions used for the solubilisation of proteins and/or peptides contain a large excess of reducing agent such as DTT, DTE, mercaptoethanol or TBP. In connection with zone electrophoresis according to the present invention it is for best results important that the thiol groups of the proteins and/or peptides are converted to mixed disulphides prior to entrance into the separation media. As discussed earlier this conversion can take place within a stacking gel or zone, but a favourable alternative is to accomplish this conversion already in connection with the protein solubilisation step. Similarly in isoelectric focusing it is favourable if the thiol groups of the proteins and/or peptides are converted to mixed disulphides prior to sample application and also that the sample applied contain a minimum of reducing agent when cathodic application or when the sample is included in the rehydration solution. Also in this case conversion of the thiol groups to mixed disulphides in connection with sample solubilisation is the best approach. In the solubilisation solutions used to accomplish this conversion, an excess of a disulphide-comprising compound according to the invention is included and this disulphide is complemented with a small, catalytic amount of reducing agent In a specific embodiment, a conventional rehydration solution that comprises reducing agent is supplemented with a disulphide-comprising compound according to the invention. The various components of rehydration solutions have been discussed in detail above in the context of the method.

A third aspect of the present invention is a reagent for use in electrophoretic separation of proteins and/or peptide components of a sample, which reagent comprises a reactive disulphide-comprising compound in solution. The solution can e.g. be aqueous, either comprising the disulphide as such or diluted in an aqueous solution. The present reagent can be used in any electrophoresis to avoid the above-discussed problems associated with the presence of thiol groups, such as zone electrophoresis, isoelectric focusing and isotachophoresis.

A fourth aspect of the present invention is a gel for electrophoresis, which comprises reactive disulphide groups. As mentioned above, the disulphide groups can be incorporated into the gel during its preparation, e.g. by adding disulphide to an agarose solution before solidification or adding it during the preparation of a polyacrylamide gel. Alternatively, a dry gel is rehydrated in a solution that comprises the disulphide-comprising compound as a pretreatment before electrophoresis.

Accordingly, a last aspect of the invention is a kit comprising a dried gel for electrophoresis and a rehydration solution in a separate compartment.

Finally, an additional aspect of the present invention is a solution for solubilisation and/or treatment of proteins and/or peptides prior to MS, which comprises an excess of a reactive disulphide-comprising compound supplemented with a small catalytic amount of reducing agent. As discussed earlier the reaction of the protein thiol groups with a disulphide-comprising compound give advantages not only in the electrophoretic separation steps, but also in the mass spectrometric identification and characterisation of proteins and/or peptides. This is due to that the reaction of thiols with disulphide has a much higher specificity than the alkylation reaction conventionally used. In the simplest embodiment, a solution for solubilisation and/or treatment of proteins prior to MS, besides the disulphide and trace amounts of reducing agent, contains a buffer such as ammonium bicarbonate. In that case, the subsequent trypsin digestion can be performed in said solution. To get and maintain the protein to characterise in solution, other additives, such as urea, guanidine hydrochloride will normally be needed, in which case the treatment normally will be followed by a desalting step prior to the digestion. If the trypsin digestion is performed without disulphide present, disulphide with trace amounts of reducing agent is added at the end of the digestion to convert all the proteins' inter and intra chain disulphide bridges to mixed disulphides prior to the mass spectrometric characterisation.

DETAILED DESCRIPTION OF THE DRAWINGS

FIG. 1 compares the results of SDS-electrophoresis experiments run according to prior art methods with the method according to the invention, where the separation is performed in a gel containing dihydroxyethyl disulphide.

FIG. 2a–e compare resulting 2-D maps with the first dimension focusing in IPG-strips pH 6–11 either with prior art methods (FIG. 2a and 2b) or containing different disulphides according to the invention (FIG. 2c: di-(2-hydroxyethyl)-disulphide; 2d: di-(3-hydroxypropyl)-disulphide; and 2e: 3-((3-amino-3oxy-propyl)-dithio) propanamide, 2f: 2,2'-dipyridyl-disulphide).

FIG. 3a–c compare resulting maps with a long narrow range IPG-strips pH 7.5–9.5 as first dimension with prior art methods (FIG. 3a) and with strips rehydrated with disulphides (FIG. 3b: di-(2-hydroxyethyl)-disulphide; and 3c: di-(3-hydroxypropyl)-disulphide).

Figure 4A:
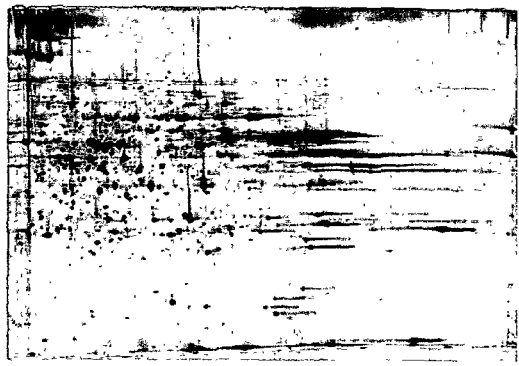
FIG. 4 a–e compare resulting 2-D maps when IPG-strip pH 6–9 have been used as first dimension with prior art methods (FIG. 4a and b), with strips rehydrated with a solution comprising an illustrative disulphide according to the invention and reduced samples applied anodic (FIG. 4c and d), respectively, with sample in which the thiol groups have been converted according to the invention prior to sample application (FIG. 4e).
Figure 4B:
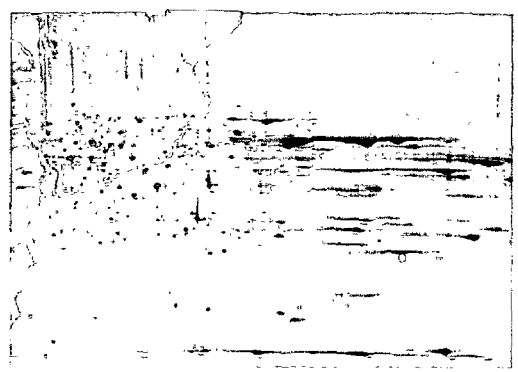
Figure 4C:
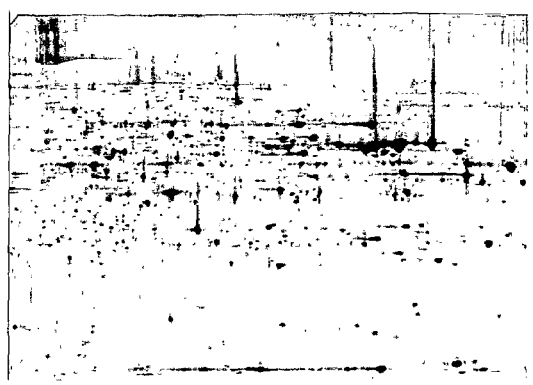
Figure 4D:
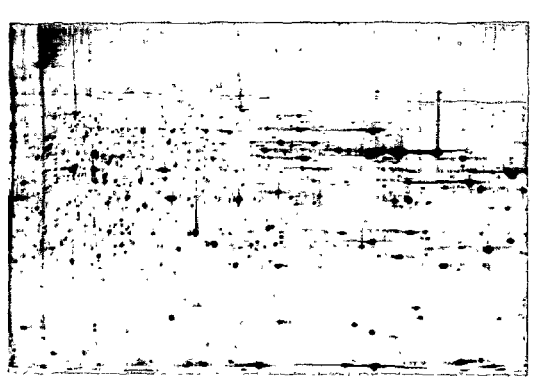
Figure 4E:
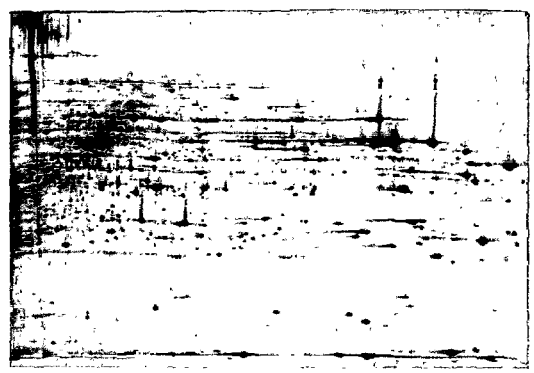

FIG. 4a–e compare resulting 2-D maps when IPG-strips pH 6–9 have been used as first dimension with prior art methods (FIG. 4a and b), with strips rehydrated with di-(2-hydroxyethyl)-disulphide and reduced samples applied anodic (FIG. 4c and d), respectively, with sample in which the thiol groups have been converted to mixed disulphides prior to sample application (FIG. 4e).

Figure 5A:
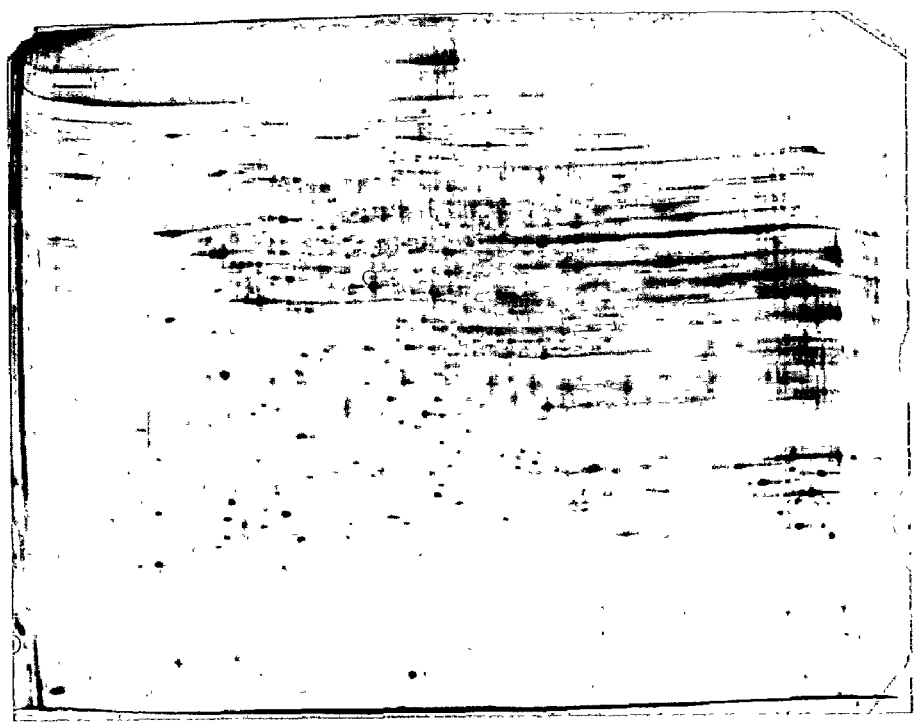
FIG. 5a and b compare resulting 2-D maps generated with IPG-strips pH 3–10 as first dimension and where the thiol groups of the proteins have been converted to mixed disulphides prior to sample application.
Figure 5B:
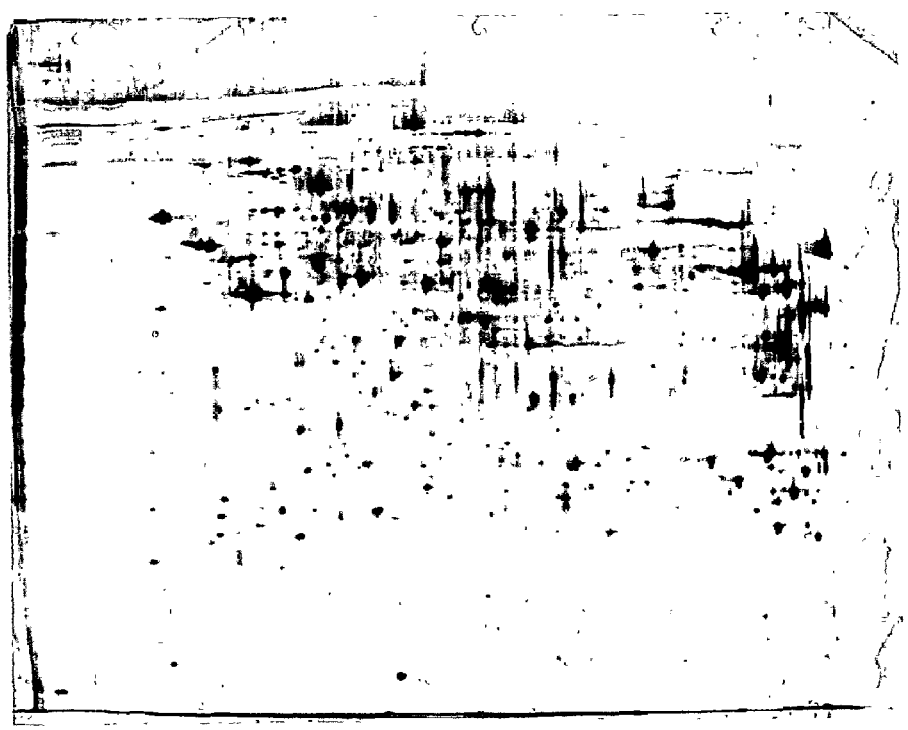
FIG. 5b shows the result for a strip rehydrated in a solution containing di-(2-hydroxyethyl)-disulphide.

FIG. 5a and b compare resulting 2-D maps generated with IPG-strips pH 3–10 as first dimension and where the thiol groups of the proteins have been converted to mixed disulphides prior to sample application. FIG. 5a shows the result when the first dimension strip neither contains any reducing agent nor any disulphide, while FIG. 5b shows the result for a strip rehydrated in a solution containing di-(2-hydroxyethyl)-disulphide.

Figure 6A:
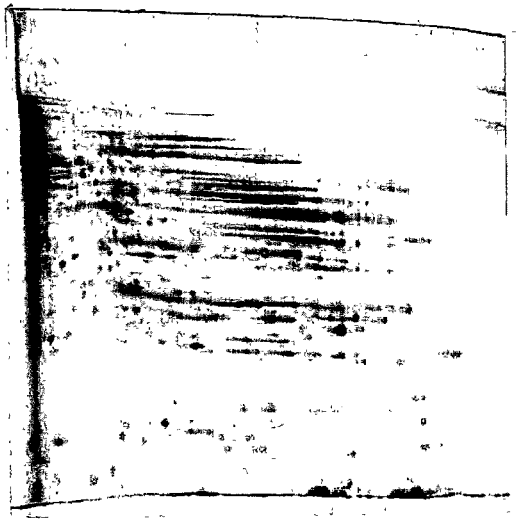
FIG. 6 a–d compare resulting 2-D maps generated with IPG-strips pH 6–11 (FIG. 6a and b) or IPG-strips pH 9–12 (FIG. 6c and d), were the samples have been included in the rehydration solution. The rehydration solutions either contained 20 mM DTT (FIGS. 6a and c) or 20 mM di-(2-hydroxyethyl)-disulphide.
Figure 6B:
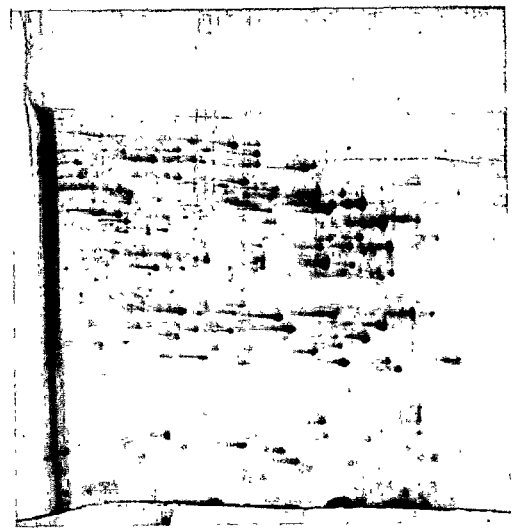
Figure 6C:
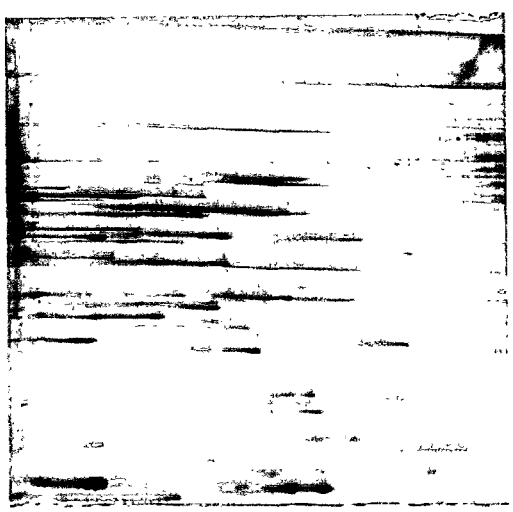
Figure 6D:
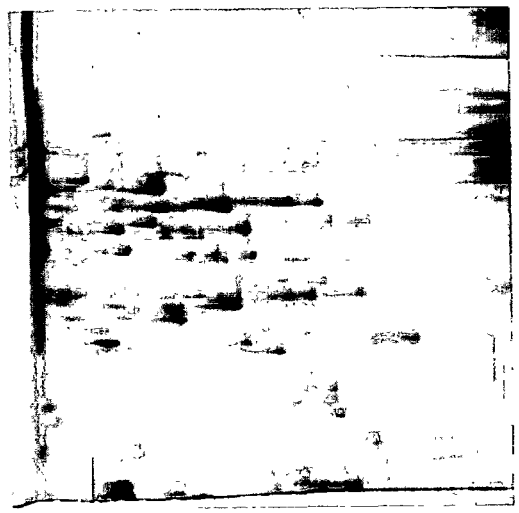

FIG. 6a–c compare resulting 2-D maps generated with IPG-strips pH 6–11 (FIGS. 6a and b) or IPG-strips pH 9–12 (FIGS. 6c and d), were the samples have been included in the rehydration solution. The rehydration solutions either contained 20 mM DTT (FIGS. 6a and c) or 20 mM di-(2-hydroxyethyl)-disulphide.

Figure 7:
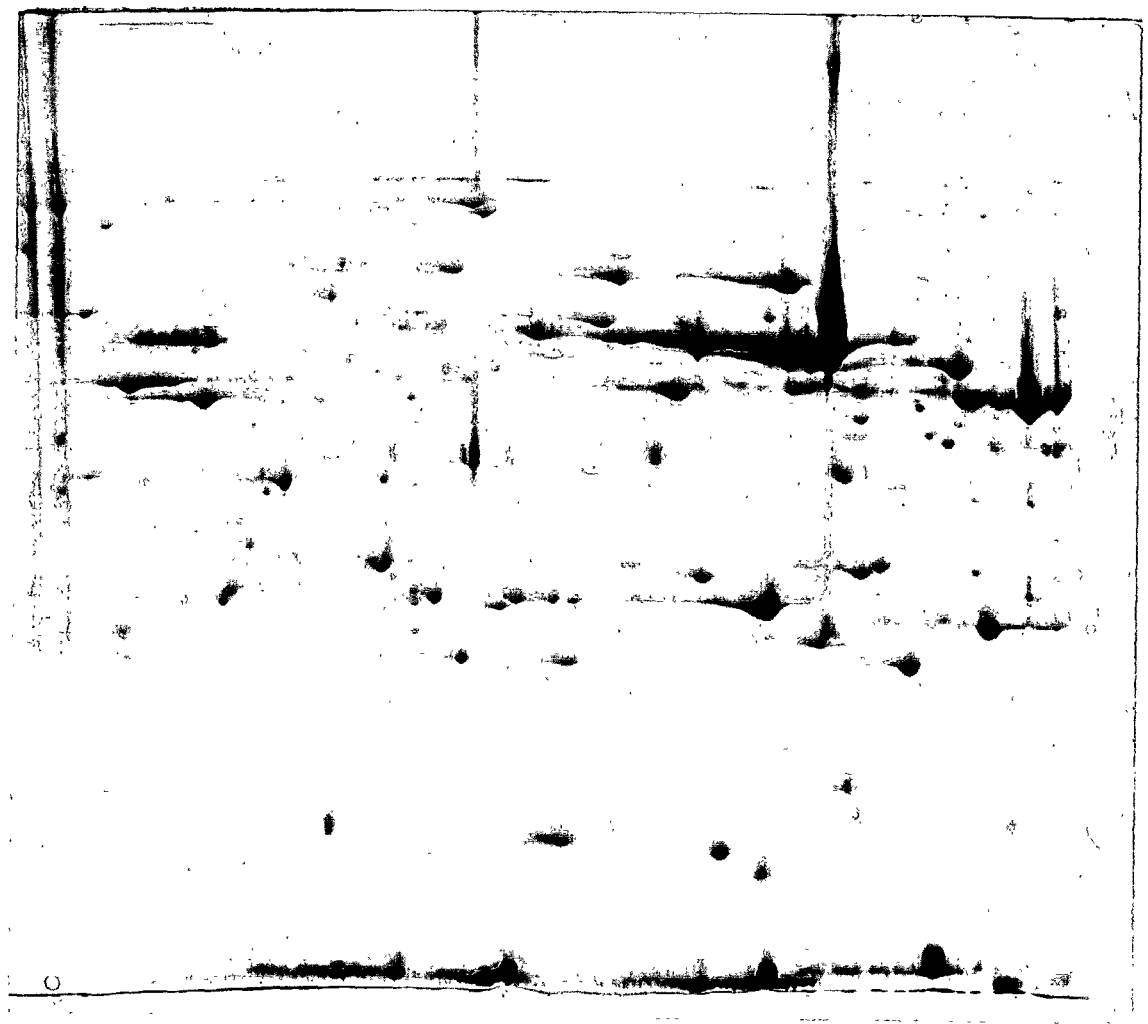
FIG. 7 shows the resulting 2-D map with a microprepative amount of protein (1.6 mg) applied anodic to a 24 cm long IPG strip pH 6–9 rehydrated in a solution containing 100 mM di-(2-hydroxyethyl)-disulphide.

FIG. 7 shows the resulting 2-D map with a micropreparative amount of protein (1.6 mg) applied anodic to a 24 cm long IPG strip pH 6–9 rehydrated in a solution containing 100 mM di-(2-hydroxyethyl)-disulphide.

Experimental Part

The present examples are provided for illustrative purposes only and are not to be construed as limiting the scope of the present invention as defined by the appended claims. All references given below and elsewhere in the present specification are hereby included by reference.

EXAMPLE 1

Clean Gel™ 25 (Amersham Biosciences, Uppsala, Sweden), a commercially available dry gel for zone electrophoresis with the dimensions 250×110×0.5 mm (after rehydration) composed of a stacking gel with T=5% (5 gram monomer/ 100 ml) and C=3% (3 gram cross-linker/ 100 gram monomer) and a separation gel with T=10 and C=2, was cut in two halves. One half was rehydrated in the rehydration solution delivered with the gel containing 0.3 M Tri-acetate buffer pH 6.5 and 0.1% SDS. The other half was rehydrated in the corresponding solution to which also bis(hydroxyethyl) disulphide had been added to a concentration of 300 mM. The two halves were placed on the cooling plate of a Multiphorm (Amersham Biosciences, Uppsala, Sweden) set to 15° C. The cathodic electrode paper wick contained Tris-tricine-SDS and the anodic paper wick contained Tris-Acetate (electrode solutions delivered with the gel). 0.3 mg/ml of the proteins bovine serum albumin, ovalbumin chicken, soybean trypsin inhibitor and bovine carbonic anhydrase were solubilised in 0.375 M Tris/HCl pH 8.8, 5% SDS and 2.5% mercaptoethanol and heated to 95° C. for 3 minutes. Half of the samples were diluted 10 times in 0.375 M Tris/HCl pH 8.8, 5% SDS and a trace of bromophenol blue, the other halves were diluted in the same buffer to which 300 mM bis(hydroxyethyl) disulphide had been added. The samples were applied to the two gel halves in the following order: bovine serum albumin lane 1, 2, 9 and 10; ovalbumin chicken lane 3 and 4; soybean trypsin inhibitor lane 5 and 6; bovine carbonic anhydrase lane 7 and 8. The electrophoretic separation was initially run with 200V, 70 mA and 40 W as maximum limitations for 10 minutes and then with 600 V, 100 mA and 40 W until the dye marking the buffer front reached the anodic wick. The gel halves were silver stained and the resulting stained gel halves are shown in FIG. 1. As can be seen from the figure, all proteins give well defined main bands, when separated in the gel half containing 300 mM dihydroxyethyl disulphide. The results were identical for reduced samples and samples to which disulphide had been added indicating that the protein thiol groups present in the reduced samples have been completely converted to mixed disulphide in an early state of the experiment, when the proteins were still stacked. The separation in the gel half without added disulphide gave good results only for carbonic anhydrase, which is a protein without thiol groups. Bovine serum albumin containing 34 thiol groups applied in reduced form give a very marked broadened band, also the sample applied after addition of disulphide give a broader band, although the effect is less pronounced than for bovine serum albumin, run in the gel half rehydrated with disulphide. The band broadening is towards the anode corresponding to the generation of protein configurations with increased electrophoretic mobilities. Ovalbumin with 6 thiol groups give with the reduced sample two bands, of which the one corresponding to an increased mobility is slightly stronger. With the sample treated with disulphide the original band is strongest and only a small fraction appear in a form with increased mobility. For the soybean trypsin inhibitor (4 thiol groups), the sample applied in the reduced form is completely in a band with high mobility, while the sample applied after disulphide addition appear in two bands with a minor fraction in the band with high mobility. Based on available knowledge generation of internal —S—S— bridges tend to result in an increase of the electrophoretic mobility of the SDS-protein complexes. The conclusion of the present experiment is that reduced samples run in a gel without disulphide oxidation of thiol groups result in either broadened band or extra artifactual bands, but also for the disulphide containing samples some negative effects of oxidation appear. While the addition of disulphide to the samples prior to application gives improvements as compared to the prior art, for best results the disulphide should be present in the gel during the separation.

Examples 2–7 were run according to standard protocols found in the 2-D handbook from Amersham Biosciences AB, Uppsala, Sweden (2-D electrophoresis using Immobilised pH gradient. Principles & methods). For the first dimension focusing, dried prefabricated gel strips (Immobiline DryStrip™, Amersham Biosciences, Uppsala, Sweden) were used with pH gradient and length as specified in the Examples 2–7. In all cases, rehydration of the strips was performed in Amersham Biosciences' Immobiline DryStrip Reswelling Tray™ according to the recommendations in the Handbook and with compositions of the different rehydration as specified in the examples beneath.

First dimension focusing were in all cases run with the gel-side up and with paper electrode wicks either in the Multiphor™ or the IPGphor™ (both equipment's from Amersham Biosciences, Uppsala, Sweden). Second dimension gels were run in the Ettan DALT™ II system with home cast acrylamide gels and the Laemmli buffer system (see above). Homogeneous gels were generated from a solution containing 12.5%(w/v) total monomer. Gels were stained with silver or Commassie Brilliant Blue as indicated.

EXAMPLE 2

Immobiline DryStrip™ pH 6–11, 18 cm were rehydrated over-night with solutions containing 8 M urea, 0.5% CHAPS, 1% IPG™ buffer pH 6–11 and redox chemicals as specified bellow. The sample extract from mouse liver containing 50 mM Tris, 7 M urea, 2 M thiourea, 4%(w/v) CHAPS and 10 mM DTT were diluted (10 μl to 160 μl) in the same solutions as used for rehydration to provide final sample concentrations of 1 mg/ml. To the correspondingly rehydrated IPG-strips 80 μl of each sample were applied in sample cups positioned close to the anodic end of the strip. The gels generated in the second dimension were silver stained and the results are shown in FIG. 2 a–f.

| Figure | Sample and rehydration solution |
|---|---|
| a | 8 M urea, 0.5% CHAPS, 1% IPGbuffer pH 6–11, 20 mM mercaptoethanol |
| b | 8 M urea, 0.5% CHAPS, 1% IPGbuffer pH 6–11, 20 mM dithiothreitol |

-continued

| Figure | Sample and rehydration solution |
|---|---|
| c | 8 M urea, 0.5% CHAPS, 1% IPGbuffer pH 6–11, 50 mM di-(2-hydroxyethyl)-disulphide |
| d | 8 M urea, 0.5% CHAPS, 1% IPGbuffer pH 6–11, 50 mM di-(3-hydroxypropyl)-disulphide |
| e | 8 M urea, 0.5% CHAPS, 1% IPGbuffer pH 6–11, 40 mM 3-((3-amino-3oxy-propyl) dithio) propan-amide |
| f | 8 M urea, 0.5% CHAPS, 1% IPGbuffer pH 6–11, 5 mM 2,2'-dipyridyl-disulphide |

As can be seen from the figures, the two strips rehydrated in thiol containing solutions generated 2-D maps characterised of heavy streaking in the focusing dimension (FIG. 2a and b). This streaking is not present in the four maps generated with IPG-strips rehydrated with disulphide containing solutions according to the invention (FIG. 2c–f).

EXAMPLE 3

Immobiline DryStrips™ pH 7.5–9.5, 24 cm were rehydrated over-night with solutions containing 8 M urea, 0.5% CHAPS, 1% IPG buffer pH 6–11 and redox chemicals as specified below. The sample containing mouse liver proteins were diluted (10 µl to 160 µl) in the same solutions as used for rehydration to final sample concentrations of 1 mg/ml. To the correspondingly rehydrated IPG-strips 80 µl of each sample were applied in sample cups positioned close to the anodic end of the strip. The gels generated in the second dimension were silver stained and the results are shown in FIGS. 3a–3b.

| Figure | Sample and rehydration solution |
|---|---|
| H | 8 M urea, 0.5% CHAPS, 1% IPGbuffer pH 8–10.5, 20 mM dithiothreitol |
| I | 8 M urea, 0.5% CHAPS, 1% IPGbuffer pH 8–10.5, 50 mM di-(2-hydroxyethyl)-disulphide |
| J | 8 M urea, 0.5% CHAPS, 1% IPGbuffer pH 8–10.5, 50 mM di-(3-hydroxypropyl)-disulphide |

The experiment shows that also that when long narrow pH range IPG strips are used, addition of disulphide according to the invention results in an efficient abolishment of streaking.

EXAMPLE 4

For this experiment, Immobiline DryStrip™ pH 6–9, 24 cm were rehydrated over-night with the solutions specified in the table below. The sample containing mouse liver proteins were diluted (5 µl to 100 µl) in the solutions also specified in the table. Samples with a volume of 100 µl (corresponding to 80 µg protein) were applied in cups positioned close to the anodic end of the IPG strips.

| Figure | Sample | Strip rehydration |
|---|---|---|
| k | 8 M urea, 0.5% CHAPS, 1% IPGbuffer pH 8–10.5, 10 mM dithiothreitol | 8 M urea, 0.5% CHAPS, 0.5% Pharmalyte pH 3–10, 0.5% IPGbuffer pH 6–11, 10 mM dithiothreitol |
| l | 8 M urea, 0.5% CHAPS, 1% IPGbuffer pH 8–10.5, 20 mM mercaptoethanol | 8 M urea, 0.5% CHAPS, 0.5% Pharmalyte pH 3–10, 0.5% IPGbuffer pH 6–11, 20 mM mercaptoethanol |
| m | 8 M urea, 0.5% CHAPS, 1% IPGbuffer pH 8–10.5, 10 mM dithiothreitol | 8 M urea, 0.5% CHAPS, 0.5% Pharmalyte pH 3–10, 0.5% IPGbuffer pH 6–11, 100 mM di-(2-hydroxyethl)-disulphide |
| n | 8 M urea, 0.5% CHAPS, 1% IPGbuffer pH 8–10.5, 20 mM mercaptoethanol | 8 M urea, 0.5% CHAPS, 0.5% Pharmalyte pH 3–10, 0.5% IPGbuffer pH 6–11, 100 mM di-(2-hydroxyethl)-disulphide |
| o | 8 M urea, 0.5% CHAPS, 1% IPGbuffer pH 8–10.5, 100 mM di-(2-hydroxyethyl)-disulphide | 8 M urea, 0.5% CHAPS, 0.5% Pharmalyte pH 3–10, 0.5% IPGbuffer pH 6–11, 100 mM di-(2-hydroxyethl)-disulphide |

Resulting 2-D maps are shown in FIG. 4a–e. The normally used conditions with DTT or mercaptoethanol as reducing agent in the strip gave heavy horisontal streaking in the basic part of the strips, from approx. pH 7 (FIGS. 4a and b). When the strip instead is rehydrated in a solution containing di-(2-hydroxyethyl) disulphide as well reduced samples (FIGS. 4c and d) as sample reacted with disulphide (FIG. 4e) gave streak free results.

EXAMPLE 5

Mouse liver proteins were diluted 20 times in 8 M urea, 2% CHAPS, 1% IPG-buffer pH 8–10.5, 10 mM dithiothreitol and 100 mM di-(2-hydroxyethyl)-disulphide. 100 µl of the resulting solution corresponding to 80 µg protein was applied with anodic cup application to Immobiline DryStrips™ pH 3–10, 24 cm rehydrated either in a solution containing only 8 M urea, 0.5% CHAPS, and 0.5% IPGT buffer pH 3–10 (resulting 2-D map in FIG. 5a) or in the same solution to which also 100 mM di-(2-hydroxyethyl)-disulphide had been added (resulting 2-D map in FIG. 5b). Based on the spot positions found in FIG. 5a, the protein thiol groups have been oxidised to mixed disulphides, but to avoid streaking in the resulting 2-D map presence of di-(2-hydroxyethyl)-disulphide in the IPG™ strip during focusing is required (FIG. 5b).

EXAMPLE 6

The sample corresponding to 80 µg were added to rehydration solution used for rehydration of Immobiline DryStrips 6–11 and 8.5–12, which had N,N'-dimethylacrylamide as monomer instead of acrylamide. Composition of used rehydration solutions specified in table. The rehydration was over night.

| Figure IPG Strip | Strip rehydration |
|---|---|
| a. pH 6–11, 11 cm | 8 M urea, 2% CHAPS, 0.5% IPG-buffer 6–11, 20 mM DTT and 80 µg liver proteins |
| b. pH 6–11, 11 cm | 8 M urea, 2% CHAPS, 0.5% IPG-buffer 6–11, 20 mM MeSSMe and 80 µg liver proteins |
| c. pH 9–12, 11 cm | 8 M urea, 2% CHAPS, 0.5% Pharmalyte 8–10.5, 20 mM DTT and 80 µg liver proteins |
| d. pH 9–12, 11 cm | 8 M urea, 2% CHAPS, 0.5% Pharmalyte 8–10.5, 20 mM MeSSMe and 80 µg liver proteins |

Resulting 2-D maps generated with first dimension strips rehydrated with solution containing dithiothreitol showed heavy streaking when the samples was introduced in the rehydration step also for short 11 cm strips (FIGS. 6a and c). Use of di-(2-hydroxyethyl)-disulphide according to the invention in the rehydration solution resulted in 2-D maps of significantly better quality with reduced horizontal streaking (FIGS. 6b and d).

EXAMPLE 7

An Immobiline DryStrip™ pH 6–9, 24 cm was rehydrated in a solution containing 8 M urea, 0.5% CHAPS, 1% IPG-buffer pH 6–11 and 100 mM di-2-hydroxyethyl)-disulphide. 100 µl of mouse liver proteins (16 mg protein/ml) in a solution: 8 M urea, 2% CHAPS, 20 mM DTT and 2% IPG™ buffer was applied in a sample cup positioned at the anodic end of the strip.

The second dimension gel was stained with Coomassie Brilliant Blue. The resulting 2-D map (FIG. 7) shows that strips rehydrated in disulphide containing solution according to the invention result in good quality 2-D maps also when large protein loads (in this case 1.6 mg) are applied to the first dimension strip.

Although a number of embodiments are described in detail by the above examples, the instant invention is not limited to such specific examples. Various modifications will be readily apparent to one of ordinary skill in the art and fall within the spirit and scope of the appended claims.

What is claimed is:

1. A method of electrophoretic separation of one or more protein and/or peptide components of a sample, which method comprises
    (a) contacting the sample with a convection stabilised separation medium;
    (b) applying a voltage across said medium; and
    (c) observing the results of the separation obtained by analysis of one or more sections of the separation medium;
wherein a disulphide-containing compound selected from the group consisting of bis-(2-hydroxyethyl) disulphide; bis-(2-hydroxypropyl) disuiphide; 3,3-dipropionamidedisulphide and 2,2'-dipyridyl disulphide is added to the separation medium or to the sample before step (a) in an amount sufficient to provide an excess of reactive disulphide groups during the separation and to prevent protein agglutination and streaking.

2. The method of claim 1, wherein the separation medium includes one or more surfaces or spaces of capillary dimensions.

3. The method of claim 1, wherein the separation medium comprises a gel.

4. The method of claim 1, wherein one or more buffers are added to keep the pH and ionic strength essentially constant in the separation medium during the electrophoresis.

5. The method of claim 4, wherein the sample is treated with a charged surfactant to mask the charge of the proteins and/or polypeptides therein before it is contacted with the separation medium and wherein the proteins and/or peptides are separated according to their molecular weight.

6. The method of claim 1, wherein a stationary pH-gradient is formed by providing charged or chargeable groups along all of the separation distance in the convection stabilized separation medium and the proteins and/or polypeptides are separated according to their isoelectric points.

7. The method of claim 6, wherein the charged or chargeable groups are non-mobile and affixed to or in a matrix.

8. The method of claim 7, wherein the matrix is the separation medium.

9. The method of claim 6, wherein the separation medium includes carrier ampholytes.

10. The method of claim 9, performed in an apparatus including at least two chambers separated from each other by at least one membrane.

11. The method of claim 1, wherein a gradient of pH and/or ionic strength is formed by providing charged or chargeable groups along a part of the separation distance in the convection stabilized separation medium and wherein the proteins and/or polypeptides are separated according to their respective transport velocities.

12. The method of claim 11, wherein the separation medium includes carrier ampholytes.

* * * * *